United States Patent [19]

Murata et al.

[11] Patent Number: 4,983,596
[45] Date of Patent: Jan. 8, 1991

[54] 3-PYRROLIDINYLTHIO-1-AZABICYCLO[3.2.0]-HEPT-2-ENE-2-CARBOXYLIC ACID DERIVATIVES AND THEIR PREPARATION

[75] Inventors: Masayoshi Murata; Hideo Tsutsumi; Keiji Matsuda; Kohji Hattori; Takashi Nakajima, all of Osaka, Japan

[73] Assignee: Fujisawa Pharmaceutical Company, Ltd., Osaka, Japan

[21] Appl. No.: 347,025

[22] Filed: May 4, 1989

[30] Foreign Application Priority Data

May 12, 1988 [GB] United Kingdom ............... 8811237

[51] Int. Cl.$^5$ ............... C07D 487/04; A61K 31/40
[52] U.S. Cl. ............................. 514/210; 540/350
[58] Field of Search ...................... 540/350; 514/210

[56] References Cited

U.S. PATENT DOCUMENTS 4,822,787 4/1989 Murata ................ 514/210

FOREIGN PATENT DOCUMENTS

| | | | |
|---|---|---|---|
| 0072710 | 2/1983 | European Pat. Off. | 514/210 |
| 0102239 | 3/1984 | European Pat. Off. | 514/210 |
| 0126587 | 11/1984 | European Pat. Off. | 514/210 |
| 0160391 | 11/1985 | European Pat. Off. | 514/210 |
| 182213 | 5/1986 | European Pat. Off. | 540/350 |
| 0243686 | 11/1987 | European Pat. Off. | 514/210 |
| 59-16892 | 1/1984 | Japan | 514/210 |

*Primary Examiner*—Robert Gerstl
*Attorney, Agent, or Firm*—Oblon, Spivak, McClelland, Maier & Neustadt

[57] ABSTRACT

The invention relates to a compound of antimicrobial activity, of the formula:

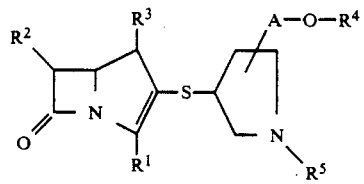

in which
  $R^1$ is carboxy or protected carboxy,
  $R^2$ is hydroxy(lower)alkyl or protected hydroxy(lower)alkyl,
  $R^3$ is hydrogen or lower alkyl,
  $R^4$ is 2-fluoroethyl, 2-chloroethyl, 2-fluoropropyl or 4-fluorobutyl,
  $R^5$ is hydrogen, lower alkanimidoyl, unsubstituted lower cycloalkenyl or substituted by a group consisting of oxo and amino, or imino-protective group, and
A is lower alkylene, or pharmaceutically acceptable salts thereof.

10 Claims, No Drawings

3-PYRROLIDINYLTHIO-1-AZABICYCLO[3.2.0]-HEPT-2-ENE-2-CARBOXYLIC ACID DERIVATIVES AND THEIR PREPARATION

The present invention relates to novel 3-pyrrolidinylthio-1-azabicyclo[3.2.0]hept-2-ene-2-carboxylic acid derivatives and pharmaceutically acceptable salts thereof.

More particularly, it relates to novel 3-pyrrolidinylthio-1-azabicyclo[3.2.0]hept-2-ene-2-carboxylic acid derivatives and pharmaceutically acceptable salts thereof, which have antimicrobial activity, to processes for the preparation thereof, to a pharmaceutical composition comprising the same, and to a use of the same as a medicament and in the treatment of infectious diseases in human being or animal.

Accordingly, one object of the present invention is to provide novel 3-pyrrolidinylthio-1-azabicyclo[3.2.0]hept-2-ene-2-carboxylic acid derivatives and pharmaceutically acceptable salts thereof, which are highly active against a number of pathogenic microorganisms and are useful as antimicrobial agents.

Another object of the present invention is to provide processes for the preparation of novel 3-pyrrolidinylthio-1-azabicyclo[3.2.0]hept-2-ene-2-carboxylic acid derivatives and salts thereof.

A further object of the present invention is to provide a pharmaceutical composition comprising, as an active ingredient, said 3-pyrrolidinylthio-1-azabicyclo[3.2.0-]hept-2-ene-2-carboxylic acid derivatives and pharmaceutically acceptable salts thereof.

Still further object of the present invention is to provide a use of said 3-pyrrolidinylthio-1-azabicyclo[3.2.0-]hept-2-ene-2-carboxylic acid derivatives and pharmaceutically acceptable salts thereof as a medicament and in the treatment of infectious diseases by pathogenic microorganisms in human being or animal.

The object 3-pyrrolidinylthio-1-azabicyclo[3.2.0-]hept-2-ene-2-carboxylic acid derivatives are novel and can be represented by the following general formula:

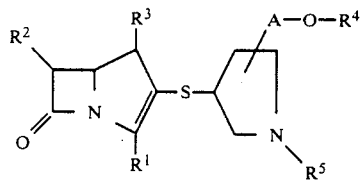
(I)

in which
$R^1$ is carboxy or protected carboxy,
$R^2$ is hydroxy(lower)alkyl or protected hydroxy(lower)alkyl,
$R^3$ is hydrogen or lower alkyl,
$R^4$ is monohalo(lower)alkyl, mono- or di(lower)alkylamino(lower)alkyl, protected mono(lower)alkylamino(lower)alkyl, mono- or di(lower)alkylcarbamoyl(lower)alkyl, or protected or unprotected carboxy(lower)alkyl,
$R^5$ is hydrogen, lower alkanimidoyl, lower cycloalkenyl which may have suitable substituent(s) or iminoprotective group, and
A is lower alkylene,
and pharmaceutically acceptable salts thereof.

Suitable pharmaceutically acceptable salts of the object compound (I) are conventional non-toxic salts and may include a salt with a base such as an inorganic base salt, for example, an alkali metal salt (e.g. sodium salt, potassium salt, etc.), an alkaline earth metal salt (e.g. calcium salt, magnesium salt, etc.), an ammonium salt, an organic base salt, for example, an organic amine salt (e.g. triethylamine salt, pyridine salt, picoline salt, ethanolamine salt, triethanolamine salt, dicyclohexylamine salt, N,N'-dibenzylethylenediamine salt, etc.); a salt with an acid such as inorganic acid addition salt (e.g. hydrochloride, hydrobromide, sulfate, phosphate, etc.), an organic acid addition salt (e.g. formate, acetate, trifluoroacetate, maleate, tartrate, methanesulfonate, benzenesulfonate, etc.); a salt with a basic or acidic amino acid (e.g. arginine, aspartic acid, glutamic acid, etc.).

In the object compound (I) and the intermediary compounds mentioned below, it is to be understood that there may be one or more stereo-isomeric pair(s) such as optical isomers due to asymmetric carbon atom(s), and such isomers are also included within the scope of the present invention.

According to the present invention, the object compound (I) or pharmaceutically acceptable salts thereof can be prepared by the processes as illustrated by the following reaction schemes.

Process 1:

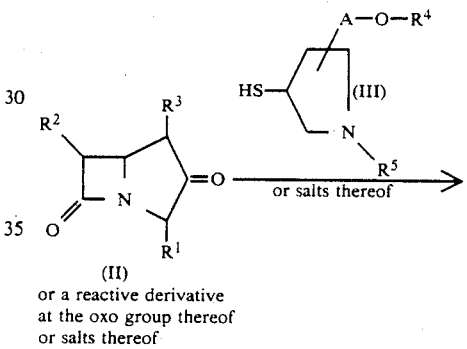

(II)
or a reactive derivative
at the oxo group thereof
or salts thereof

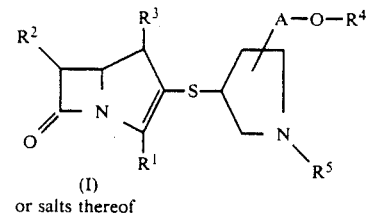

(I)
or salts thereof

Process 2:

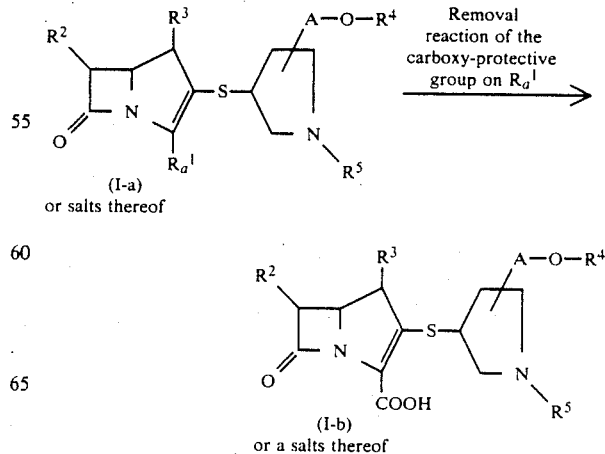

(I-a)
or salts thereof

Removal reaction of the carboxy-protective group on $R_a^1$ (I-b)
or a salts thereof Process 3:

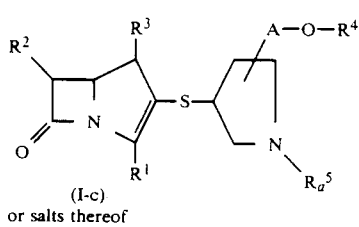

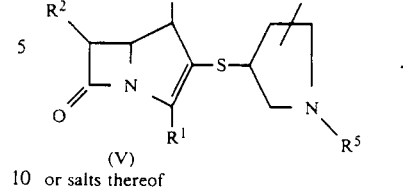

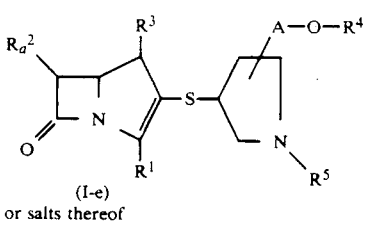

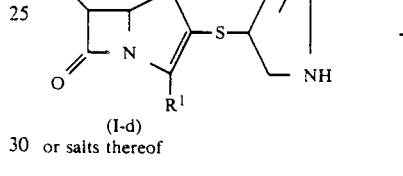

Process 4:

Process 7:

Process 5:

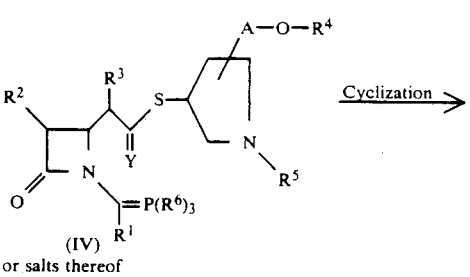

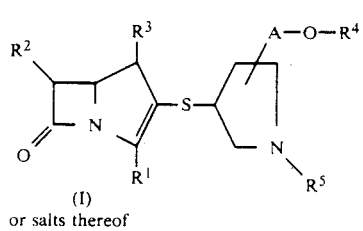

Process 6:

in which

R¹, R², R³, R⁴, R⁵ and A are each as defined above, $R_a^1$ is protected carboxy, $R_a^2$ is protected hydroxy(lower)alkyl, $R_b^2$ is hydroxy(lower)alkyl, $R_a^4$ is monohalo(lower)alkyl, $R_a^5$ is imino-protective group, $R_b^5$ is lower alkanimidoyl or lower cycloalkenyl which may have suitable substituent(s), R⁶ is aryl or lower alkoxy, R⁷ is hydroxy(lower)alkyl, Y is oxo or thioxo, and L is a leaving group.

The compound (V) used in the Process 6 can be prepared in substantially the same manner as that of Process 1.

The compounds (III) and (IV) used in the Processes 1 and 5 are new and can be prepared, for example, by the following methods or a conventional manner.

Method A:

-continued

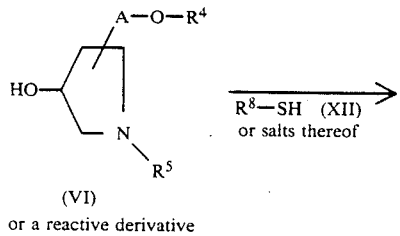

(VI)
or a reactive derivative
at the hydroxy group
thereof or salts thereof $\xrightarrow{R^8-SH \ (XII) \text{ or salts thereof}}$

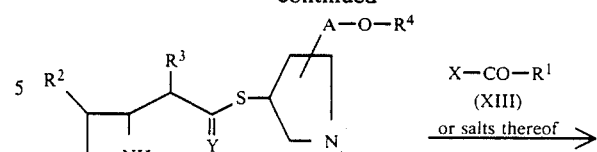

(III-a)
or salts thereof

Method B:

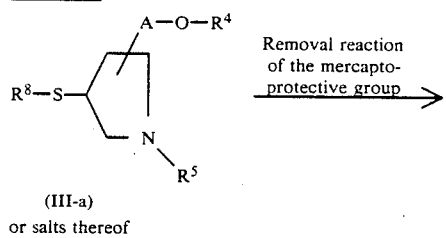

(III-a)
or salts thereof $\xrightarrow{\text{Removal reaction of the mercapto-protective group}}$

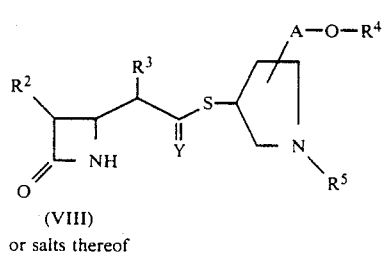

(III)
or salts thereof

Method C:

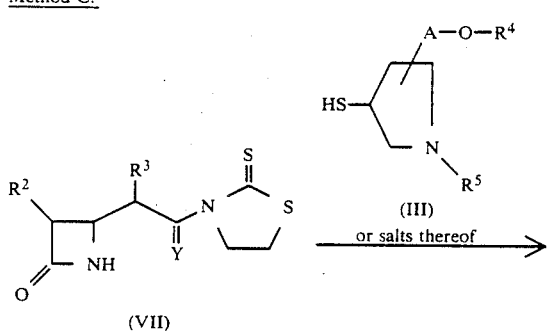

Method D:

-continued

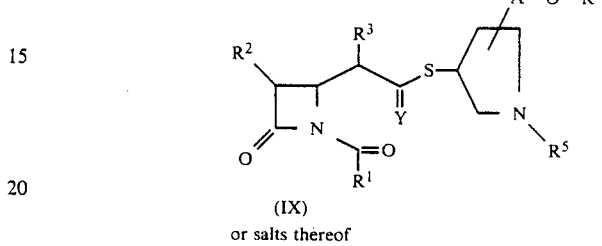

(VIII)
or salts thereof $\xrightarrow{X-CO-R^1 \ (XIII) \text{ or salts thereof}}$

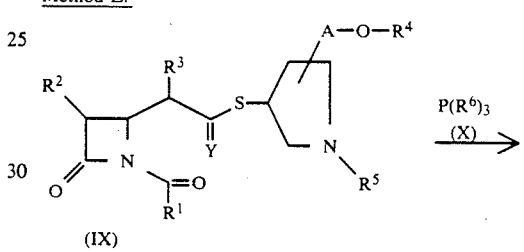

(IX)
or salts thereof

Method E:

(IX)
or salts thereof $\xrightarrow{P(R^6)_3 \ (X)}$ (IV)
or salts thereof in which
$R^1$, $R^2$, $R^3$, $R^4$, $R^5$, $R^6$, A and Y are each as defined above,
$R^8$ is mercapto-protective group, and
X is halogen.

In the above and subsequent descriptions of the present specification, suitable examples and illustrations of the various definitions which the present invention includes within the scope thereof are explained in detail as follows.

The term "lower" is intended to mean 1 to 6 carbon atom(s), unless otherwise indicated.

Suitable "protected carboxy" may include esterified carboxy wherein "esterified carboxy" can be referred to the ones as mentioned below.

Suitable examples of the ester moiety of an esterified carboxy may be the ones such as lower alkyl ester (e.g. methyl ester, ethyl ester, propyl ester, isopropyl ester, butyl ester, isobutyl ester, t-butyl ester, pentyl ester, hexyl ester, etc.) which may have at least one suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1-(or 2-)acetoxyethyl ester, 1-(or 2- or 3-)acetoxypropyl ester, 1-(or 2- or 3- or 4-)acetoxybutyl ester, 1-(or 2-)propionyloxyethyl ester, 1-(or 2- or 3-)propionyloxypropyl ester, 1-(or 2-)butyryloxyethyl ester, 1-(or 2-)isobutyryloxyethyl ester, 1-(or 2-)pyvaloyloxyethyl ester, 1-(or 2-)hexanoyloxyethyl ester, isobutyryloxymethyl ester, 2-ethylbutyryloxymethyl ester, 3,3-dimethylbutyryloxymethyl ester, 1-(or 2-)pentanoyloxyethyl ester, etc.], lower alkanesulfonyl(lower)alkyl ester (e.g. 2-mesylethyl ester, etc.), mono(or di or tri)halo{lower)alkyl ester (e.g. 2-iodoethyl ester, 2,2,2-trichloroethyl ester, etc.); lower alkoxycarbonyloxy(lower)alkyl ester [e.g. methoxycarbonyloxymethyl ester, ethoxycarbonyloxymethyl ester, propoxycarbonyloxymethyl ester, t-butoxycarbonyloxymethyl ester, 1-(or 2-)methoxycarbonyloxyethyl ester, 1-(or 2-)ethoxycarbonyloxyethyl ester, 1-(or 2-) isopropoxycarbonyloxyethyl ester, etc.], phthalidylidene(lower)alkyl ester, or (5-lower alkyl-2-oxo-1,3-dioxol-4-yl)(lower)alkyl ester [e.g. (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.]; lower alkenyl ester (e.g. vinyl ester, allyl ester, etc.); lower alkynyl ester (e.g. ethynyl ester, propynyl ester, etc.); ar(lower)alkyl ester which may have at least one suitable substituent(s) such as mono- or di- or triphenyl[lower)alkyl ester which may have halogen or lower alkoxy (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.); aryl ester which may have at least one suitable substituent(s) (e.g. phenyl ester, 4-chlorophenyl ester, tolyl ester, t-butylphenyl ester, xylyl ester, mesityl ester, cumenyl ester, etc.); phthalidyl ester; and the like.

More preferable example of the protected carboxy thus defined may be $C_2$–$C_4$ alkenyloxycarbonyl and phenyl(or nitrophenyl)($C_1$–$C_4$)alkoxycarbonyl, and the most preferable one may be allyloxycarbonyl and 4-nitrobenzyloxycarbonyl.

Suitable "hydroxy(lower)alkyl" may include straight or branched lower alkyl having hydroxy group such as hydroxymethyl, hydroxyethyl, hydroxypropyl, 1-(hydroxymethyl)ethyl, 1-hydroxy-1-methylethyl, hydroxybutyl, hydroxypentyl, hydroxyhexyl, and the like, in which more preferable example may be hydroxy($C_1$–$C_4$)alkyl and the most preferable one may be 1-hydroxyethyl for $R^2$ and 2-hydroxyethyl for $R^7$.

Suitable "protected hydroxy(lower)alkyl" means aforementioned hydroxy(lower)alkyl, in which the hydroxy group is protected by a conventional hydroxy-protective group such as those mentioned in the explanation of imino-protective group as mentioned below; ar(lower)alkyl such as mono- or di- or triphenyl(lower)alkyl (e.g. benzyl, benzhydryl, trityl, etc.), etc.; trisubstituted silyl such as tri(lower)alkylsilyl (e.g. trimethylsilyl, triethylsilyl, isopropyldimethylsilyl, t-butyldimethylsilyl, diisopropylmethylsilyl, etc.), triarylsilyl (e.g. triphenylsilyl, etc.), triarl(lower)alkylsilyl (e.g. tribenzylsilyl, etc.), etc.; and the like.

More preferable example of "protected hydroxy(lower)alkyl thus defined may be [phenyl(or nitrophenyl)($C_1$–$C_4$)alkoxy]carbonyloxy($C_1$–$C_4$)alkyl, ($C_2$–$C_4$)alkenyloxycarbonyloxy($C_1$–$C_4$)alkyl and [tri($C_1$–$C_4$)alkylsilyl]oxy($C_1$–$C_4$)alkyl, and the most preferable one may be 1-(allyloxycarbonyloxy)ethyl and 1-(t-butyldimethylsilyloxy)ethyl.

Suitable "lower alkyl" may include straight or branched one such as methyl, ethyl, propyl, isopropyl, butyl, t-butyl, pentyl, hexyl, and the like, in which more preferable example may be $C_1$–$C_4$ alkyl and the most preferable one may be methyl.

Suitable "monohalo(lower)alkyl" means straight or branched lower alkyl as mentioned above, which has one halogen atom (e.g. chlorine, bromine, iodine, fluorine), and suitable example thereof may include chloromethyl, fluoromethyl, bromomethyl, iodomethyl, chloroethyl, bromoethyl, fluoroethyl, 1-(chloromethyl)ethyl, 1-(fluoromethyl)ethyl, chloropropyl, fluoropropyl, fluorobutyl, fluoropentyl, fluorohexyl, and the like, in which more preferable example may be monohalo($C_1$–$C_4$)alkyl and the most preferable one may be 2-fluoroethyl, 2-chloroethyl, 2-fluoropropyl and 4-fluorobutyl.

Suitable "mono- or di(lower)alkylamino(lower)alkyl" means straight or branched lower alkyl as mentioned above, which has straight or branched, mono- or di(lower)alkylamino group such as methylamino, dimethylamino, ethylamino, diethylamino, N-methyl-N-ethylamino, propylamino, dipropylamino, isopropylamino, butylamino, pentylamino, hexylamino, and the like. More preferable example of mono- or di(lower)alkylamino(lower)alkyl thus defined may be mono- or di($C_1$–$C_4$)alkylamino($C_1$–$C_4$)alkyl and the most preferable one may be 2-(methylamino)ethyl and 2-(dimethylamino)ethyl.

Suitable "protected mono(lower)alkylamino(lower)alkyl means aforementioned mono(lower)alkylamino(lower)alkyl, in which the amino group is protected by a conventional amino-protective group such as those exemplified for the hydroxy-protective group in the explanation of the "protected hydroxy(lower)alkyl" as mentioned above, wherein more preferable example of amino-protective group may be phenyl(or nitrophenyl)($C_1$–$C_4$)alkoxycarbonyl and the most preferable one may be 4-nitrobenzyloxycarbonyl.

Preferable example of protected mono[lower)alkylamino(lower)alkyl thus defined may be N-(lower)alkyl-N-nitrophenyl(lower)alkoxycarbonylamino(lower)alkyl and more preferable one may be N-($C_1$–$C_4$)alkyl-N-(4-nitrobenzyloxycarbonyl)amino($C_1$–$C_4$)alkyl and the most preferable one may be 2-[N-methyl-N-(4-nitrobenzyloxycarbonyl)amino]ethyl.

Suitable "mono- or di(lower)alkylcarbamoyl(lower)alkyl" means straight or branched lower alkyl as mentioned above, which has straight or branched, mono- or di(lower)alkylcarbamoyl group such as methylcarbamoyl, dimethylcarbamoyl, ethylcarbamoyl, diethylcarbamoyl, N-methyl-N-ethylcarbamoyl, propylcarbamoyl, dipropylcarbamoyl, isopropylcarbamoyl, butylcarbamoyl, pentylcarbamoyl, hexylcarbamoyl, and the like.

More preferable example of mono- or di(lower)alkylcarbamoyl(lower)alkyl thus defined may be mono- or di($C_1$–$C_4$)alkylcarbamoyl($C_1$–$C_4$)alkyl and the most preferable one may be (methylcarbamoyl)methyl and (dimethylcarbamoyl)methyl.

Suitable "carboxy(lower)alkyl" means straight or branched lower alkyl as mentioned above, which has carboxy group such as carboxymethyl, carboxyethyl, carboxypropyl, 1-(carboxymethyl)ethyl, 1-carboxy-1-methylethyl, carboxybutyl, carboxypentyl, carboxyhexyl, and the like, in which more preferable example may be carboxy($C_1$–$C_4$)alkyl and the most preferable one may be carboxymethyl.

Suitable "protected carboxy(lower)alkyl" means aforementioned carboxy(lower)alkyl, in which the carboxy group is protected by a conventional carboxy-protective group to form so-called "esterified carboxy" as exemplified in the explanation of "protected carboxy" as mentioned above. Preferable example of protected carboxy(lower)alkyl thus defined may be lower alkenyloxycarbonyl(lower)alkyl and mono- or di- or triphenyl(lower)alkoxycarbonyl(lower)alkyl, which may have nitro or lower alkoxy, more preferable one may be ($C_2$–$C_4$)alkenyloxycarbonyl($C_1$–$C_4$)alkyl and phenyl(or nitrophenyl)($C_1$–$C_4$)alkoxycarbonyl($C_1$–$C_4$)alkyl, and the most preferable one may be allyloxycarbonylmethyl.

Suitable "imino-protective group" may include acyl such as carbamoyl, aliphatic acyl, aromatic acyl, heterocyclic acyl and aliphatic acyl substituted with aromatic or heterocyclic group(s) derived from carboxylic, carbonic, sulfonic and carbamic acids.

The aliphatic acyl may include saturated or unsaturated, acyclic or cyclic ones, for example, alkanoyl such as lower alkanoyl (e.g. formyl, acetyl, propionyl, butyryl, isobutyryl, valeryl, isovaleryl, pivaloyl, hexanoyl, etc.), alkylsulfonyl such as lower alkylsulfonyl (e.g. mesyl, ethylsulfonyl, propylsulfonyl, isopropylsulfonyl, butylsulfonyl, isobutylsulfonyl, pentylsulfonyl, hexylsulfonyl, etc.), carbamoyl, N-alkylcarbamoyl [e.g. methylcarbamoyl, ethylcarbamoyl, etc.), alkoxycarbonyl such as lower alkoxycarbonyl (e.g. methoxycarbonyl, ethoxycarbonyl, propoxycarbonyl, butoxycarbonyl, t-butoxycarbonyl, etc.), alkenyloxycarbonyl such as lower alkenyloxycarbonyl (e.g. vinyloxycarbonyl, allyloxycarbonyl, etc.), alkenoyl such as lower alkenoyl (e.g. acryloyl, methacryloyl, crotonoyl, etc.), cycloalkanecarbonyl such as cyclo(lower)alkanecarbonyl (e.g. cyclopropanecarbonyl, cyclopentanecarbonyl, cyclohexanecarbonyl, etc.), and the like.

The aliphatic acyl substituted with aromatic group(s) may include ar(lower)alkoxycarbonyl such as phenyl(lower)alkoxycarbonyl (e.g. benzyloxycarbonyl, phenethyloxycarbonyl, etc.), and the like.

These acyl groups may be further substituted with one or more suitable substituent(s) such as nitro, and the like, and preferable acyl having such substituent(s) may be nitroar(lower)alkoxycarbonyl(e.g. nitrobenzyloxycarbonyl, etc.), and the like.

Preferable example of "imino-protective group" thus defined may be lower alkenyloxycarbonyl and phenyl(or nitrophenyl)(lower)alkoxycarbonyl, more preferable one may be ($C_2$–$C_4$) alkenyloxycarbonyl and phenyl(or nitrophenyl)($C_1$–$C_4$)alkoxycarbonyl, and the most preferable one may be allyloxycarbonyl and 4-nitrobenzyloxycarbonyl.

Suitable "lower alkylene" may include straight or branched one such as methylene, ethylene, trimethylene, tetramethylene, pentamethylene, hexamethylene, methylmethylene, ethylethylene, propylene, and the like, in which more preferable example may be $C_1$–$C_4$ alkylene and the most preferable one may be methylene.

Suitable "mercapto-protective group" may include acyl as mentioned above, ar(lower)alkyl such as mono- or di- or triphenyl(lower)alkyl (e.g. benzyl, phenethyl, benzhydryl, trityl, etc.), and the like, in which more preferable example may be $C_1$–$C_4$ alkanoyl, aroyl and triphenyl($C_1$–$C_4$)alkyl, and the most preferable one may be acetyl.

Suitable "lower alkanimidoyl" may be straight or branched one such as formimidoyl, acetimidoyl, propionimidoyl, butyrimidoyl, isovalerimidoyl, pentanimidoyl, hexanimidoyl, and the like, in which more preferable one may be ($C_1$–$C_4$)alkanimidoyl and the most preferable one may be formimidoyl.

Suitable "aryl" may include phenyl, tolyl, xylyl, cumenyl, mesithyl, naphthyl and the like, in which more preferable example may be $C_6$–$C_{10}$ aryl and the most preferable one may be phenyl.

Suitable "lower alkoxy" may include straight or branched one such as methoxy, ethoxy, propoxy, isopropoxy, butoxy, isobutoxy, pentyloxy, isopentyloxy, hexyloxy, etc., in which more preferable example may be $C_1$–$C_4$ alkoxy and the most preferable one may be ethoxy.

Suitable "halogen" may include chlorine, bromine, iodine and fluorine, in which more preferable example may be chlorine.

Suitable "leaving group" may include ar(lower)alkoxy such as phenyl(lower)alkoxy (e.g. benzyloxy, etc.), etc.; lower alkoxy (e.g. ethoxy, etc.); halogen (e.g. chlorine, bromine, iodine, etc.); acyloxy such as lower alkanoyloxy (e.g. acetoxy, etc.), sulfonyloxy (e.g. methanesulfonyloxy, benzenesulfonyloxy, toluenesulfonyloxy, etc.), etc.; or the like.

Suitable "lower cycloalkenyl" moiety of "lower cycloalkenyl which may have suitable substituent(s)" may be $C_3$–$C_6$ cycloalkenyl such as cyclopropenyl, cyclobutenyl, cyclopentenyl, cyclohexenyl, cyclopentadienyl, cyclohexadienyl, and the like, wherein said lower cycloalkenyl moiety may have suitable substituent(s) such as oxo, amino, protected amino wherein the amino-protective group is as mentioned above, and the like.

More preferable example of "lower cycloalkenyl which may have suitable substituents" thus defined may be 3-oxo-1-cycloalken-1-yl having $C_4$–$C_6$ carbon atoms, which may be substituted by suitable substitutent(s) selected from a group consisting of amino and oxo, and the most preferable one may be 2-amino-3,4-dioxo-1-cyclobuten-1-yl.

The processes for the preparation of the object compound (I) of the present invention are explained in detail in the following. (1) Process 1

The compound (I) or salts thereof can be prepared by reacting the compound (II) or a reactive derivative at the oxo group thereof or salts thereof with the compound (III) or salts thereof.

Suitable salts of the compound (II) may be salts with bases such as those given for the compound (I).

The reactive derivative at the oxo group of the compound (II) can be represented by the following formula (II'), which is preferably used in this reaction and can be prepared by reacting the compound (II) or salts thereof with an acylating agent.

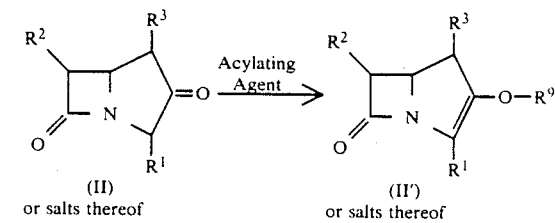

(II)
or salts thereof (II')
or salts thereof in which $R^1$, $R^2$ and $R^3$ are each as defined above, and $R^9$ is acyl as exemplified for the imino-protective group and further O,O-substituted phosphono derived from, for example, organic phosphoric acid mentioned hereinbelow.

Suitable acylating agents may include conventional ones which can introduce the acyl group as mentioned above into the compound (II), and preferable acylating agents may be organic sulfonic or phosphoric acid or its reactive derivative such as acid halide, acid anhydride, and the like, for example, arenesulfonyl halide (e.g. benzenesulfonyl chloride, p-toluenesulfonyl chloride, p-nitrobenzenesulfonyl chloride, p-bromobenzenesulfonyl chloride, etc.), arenesulfonic anhydride (e.g. benzenesulfonic anhydride, p-toluenesulfonic anhydride, p-nitrobenzenesulfonic anhydride, etc.), lower alkanesulfonyl halide which may have additional halogen (e.g. methanesulfonyl chloride, ethanesulfonyl chloride, trifluoromethanesulfonyl chloride, etc.), lower alkanesulfonic anhydride which may have halogen (e.g. methanesulfonic anhydride, ethanesulfonic anhydride, trifluoromethanesulfonic anhydride, etc.), di(lower)alkyl phosphorohaloridate (e.g. diethyl phosphorochloridate, etc.), diaryl phosphorohaloridate (e.g. diphenyl phosphorochloridate, etc.), and the like.

This acylation reaction is usually carried out in a conventional solvent which does not adversely influence the reaction such as acetone, dioxane, acetonitrile, chloroform, dichloromethane, hexamethylphosphoramide, dichloroethane, tetrahydrofuran, ethyl acetate, dimethylsulfoxide, N,N-dimethylformamide, pyridine, etc., or a mixture thereof.

When the acylating agent is used in a free acid form or its salt form in this reaction, the reaction is preferably carried out in the presence of a conventional condensing agent such as carbodiimide compound [e.g. N,N'-diethylcarbodiimide, N,N'-diisopropylcarbodiimide, N,N'-dicyclohexylcarbodiimide, N-cyclohexyl-N'-morpholinoethylcarbodiimide, N-cyclohexyl-N'-(4-diethylaminocyclohexyl)carbodiimide, N-ethyl-N'-(3-dimethylaminopropyl)carbodiimide, etc.]; N,N'-carbonyldiimidazole, N,N'-carbonylbis(2-methylimidazole); keteneimine compound (e.g. pentamethyleneketene-N-cyclohexylimine, diphenylketene-N-cyclohexylimine, etc.); ethoxyacetylene; 1-alkoxy-1-chloroethylene; ethyl polyphosphate; isopropylpolyphosphate; phosphorus oxychloride; phosphorus trichloride; thionyl chloride; oxalyl chloride; a combination of triphenylphosphine with carbon tetrachloride or diazenedicarboxylate; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorus oxychloride, etc.; and the like.

This acylation reaction may be carried out in the presence of an inorganic or organic base such as an alkali metal bicarbonate (e.g. sodium bicarbonate, potassium bicarbonate, etc.), alkali metal carbonate (e.g. sodium carbonate, potassium carbonate, etc.) alkaline earth metal carbonate (e.g. magnesium carbonate, calcium carbonate, etc.), tri(lower)alkylamine (e.g. trimethylamine, triethylamine, N,N-diisopropyl-N-ethylamine, etc.), pyridine compound [e.g. pyridine, picoline, lutidine, N,N-di(lower)alkylaminopyridine such as N,N-dimethylaminopyrinide, etc.], quinoline, N-lower alkylmorpholine (e.g. N-methylmorpholine, etc.), N,N-di(lower alkylbenzylamine (e.g. N,N-dimethylbenzylamine, etc.), alkali metal alkoxide (e.g. sodium methoxide, sodium ethoxide, potassium butoxide, etc.), and the like.

The reaction temperature of this acylation reaction is not critical and the reaction is usually carried out under from cooling to warming.

With regard to the compound (II), it is to be noted that the 3,7-dioxo-1-azabicyclo[3.2.0]heptane ring system of the following formula (IIA) is well known to lie to tautomeric relation with the 3-hydroxy-7-oxo-1-azabicyclo[3.2.0]hept-2-ene ring system of the following formula (IIB), and accordingly, it is to be understood that both of these ring systems are substantially the same.

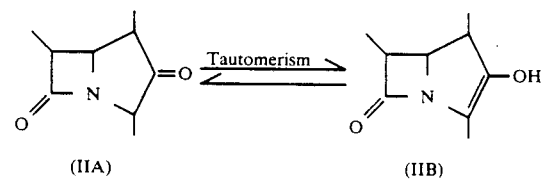

(IIA)  (IIB)

The compound (II') or salts thereof can be used with or without isolation for the subsequent reaction with the compound (III) or salts thereof.

Suitable salts of the compound (III) may be the same as those for the compound (I) and silver salt.

The reaction of the compound (II) or its reactive derivative or salts thereof with the compound (III) or salts thereof can be carried out in the presence of an organic or inorganic base such as those given in the explanation of the acylation reaction as stated above.

This reaction can be carried out in a conventional solvent which does not adversely influence the reaction such as those given in the explanation of the acylation reaction.

The reaction temperature is not critical and the reaction is usually carried out under from cooling to warming.

(2) Process 2

The compound (I-b) or salts thereof can be prepared by subjecting the compound (I-a) or salts thereof to removal reaction of the carboxy-protective group on $R_a^1$.

Suitable salts of the compounds (I-a) and (I-b) may be the same as those for the compound (I).

The present reaction is usually carried out by a conventional method such as hydrolysis, reduction, and the like.

(i) Hydrolysis:

Hydrolysis is preferably carried out in the presence of a base or an acid. Suitable base may include an alkali-metal hydroxide (e.g. sodium hydroxide, potassium hydroxide, etc.), an alkaline earth metal hydroxide (e.g. magnesium hydroxide, calcium hydroxide, etc.), alkali metal hydride (e.g. sodium hydride, potassium hydride, etc.), alkaline earth metal hydride (e.g. calcium hydride, etc.), alkali metal alkoxide (e.g. sodium methoxide, sodium ethoxide, potassium t-butoxide, etc.), an alkali metal carbonate (e.g. sodium carbonate, potassium carbonate, etc.), and alkaline earth metal carbonate (e.g. magnesium carbonate, calcium carbonate, etc.), an alkali metal bicarbonate (e.g. sodium bicarbonate, potassium bicarbonate, etc.), and the like.

Suitable acid may include an organic acid (e.g. formic acid, acetic acid, propionic acid, trifluoroacetic acid, benzenesulfonic acid, p-toluenesulfonic acid, etc.) and an inorganic acid (e.g. hydrochloric acid, hydrobromic acid, sulfuric acid, phosphoric acid, etc.). The acidic hydrolysis using trifluoroacetic acid is usually accelerated by addition of cation trapping agent (e.g. phenol, anisole, etc.).

In case that the hydroxy-protective group is tri(lower)alkylsilyl, the hydrolysis can be carried out in the presence of tri(lower)alkylammonium halide (e.g. tributylammonium fluoride, etc.).

This reaction is usually carried out in a conventional solvent which does not adversely influence the reaction such as water, dichloromethane, alcohol (e.g. methanol, ethanol, etc.), tetrahydrofuran, dioxane, acetone, etc., or a mixture thereof. A liquid base or acid can be also used as the solvent.

The reaction temperature is not critical and the reaction is usually carried out under from cooling to heating.

(ii) Reduction:

The reduction method applicable for this removal reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, sulfuric acid, etc.); and conventional catalytic reduction in the presence of a conventional metallic catalyst such as palladium catalysts (e.g. spongy palladium, palladium black, palladium oxide, palladium on carbon, colloidal palladium, palladium on barium sulfate, palladium on barium carbonate, palladium hydroxide on carbon, etc.), nickel catalysts (e.g. reduced nickel, nickel oxide, Raney nickel, etc.), platinum catalysts (e.g. platinum plate, spongy platinum, platinum black, colloidal platinum, platinum oxide, platinum wire, etc.), and the like.

In case that the catalytic reduction is applied, the reaction is preferably carried out around neutral condition.

This reaction is usually carried out in a conventional solvent which does not adversely influence the reaction such as water, alcohol (e.g. methanol, ethanol, propanol, etc.), dioxane, tetrahydrofuran, acetic acid, buffer solution (e.g. phosphate buffer, acetate buffer, etc.), and the like, or a mixture thereof.

The reaction temperature is not critical and the reaction is usually carried out under from cooling to warming.

In case that the carboxy-protective group is allyl group, it can be deprotected by hydrogenolysis using a palladium compound.

Suitable palladium compound used in this reaction may be palladium on carbon, palladium hydroxide on carbon, palladium chloride, a palladium-ligand complex such as tetrakis(triphenylphosphine)palladium(O), bis(dibenzylideneacetone)palladium(O), di[1,2-bis(diphenylphosphino)ethane]palladium(O), tetrakis(triphenyl phosphite)palladium(O), tetrakis(triethyl phosphite)palladium(O), and the like.

The reaction can preferably be carried out in the presence of a scavenger of allyl group generated in situ, such as amine (e.g. morpholine, N-methylaniline, etc.), an activated methylene compound (e.g. dimedone, benzoylacetate, 2-methyl-3-oxovaleric acid, etc.), a cyanohydrin compound (e.g. O-tetrahydropyranyloxybenzyl cyanide, etc.), alkanoic acid or a salt thereof (e.g. formic acid, acetic acid, ammonium formate, sodium acetate, sodium 2-ethylhexanoate, etc.), N-hydroxysuccinimide, and the like.

This reaction can be carried out in the presence of a base such as lower alkylamine (e.g. butylamine, triethyamine, etc.), pyridine, and the like.

When palladium-ligand complex is used in this reaction, the reaction can preferably be carried out in the presence of the corresponding ligand (e.g. triphenylphosphine, triphenyl phosphite, triethyl phosphite, etc.).

This reaction is usually carried out in a conventional solvent which does not adversely influence the reaction such as water, methanol, ethanol, propanol, dioxane, tetrahydrofuran, acetonitrile, chloroform, dichloromethane, dichloroethane, ethyl acetate, etc., or a mixture thereof.

The removal reaction can be selected according to the kind of carboxy-protective group to be removed.

The present process includes within the scope thereof a case that the hydroxy- protective group on $R^2$, amino- and/or carboxy-protective group(s) on $R^4$, and/or imino-protective group of $R^5$ are removed at the same time during the reaction.

(3) Process 3:

The compound (I-d) or salts thereof can be prepared by subjecting the compound (I-c) or salts thereof to removal reaction of the imino-protective group on $R_a^5$.

Suitable salts of the compounds (I-c) and (I-d) may be the same as those for the compound (I).

This reaction is usually carried out by a conventional method such as hydrolysis, reduction and the like.

The method of hydrolysis and reduction, and the reaction conditions (e.g. reaction temperature, solvent, etc.) are substantially the same as those illustrated for removal reaction of the carboxy-protective group of the compound (I-a) in Process 2, and therefore are to be referred to said explanation.

The present process includes within the scope thereof a case that the carboxy- and/or hydroxy- and/or amino-protective group(s) on $R^1$ and/or $R^2$ and/or $R^4$ are removed at the same time during the reaction.

(4) Process 4:

The compound (I-f) or salts thereof can be prepared by subjecting the compound (I-e) or salts thereof to removal reaction of the hydroxy-protective group on $R_a^2$.

Suitable salts of the compounds (I-e) and (I-f) may be the same as those for the compound (I).

This reaction is usually carried out by a conventional method such as hydrolysis, reduction, and the like.

The method of hydrolysis and reduction, and the reaction conditions (e.g. reaction temperature, solvent, etc.) are substantially the same as those illustrated for removal reaction of the carboxy-protective group of the compound (I-a) in Process 2, and therefore are to be referred to said explanation.

In case that the hydroxy-protective group is tri(lower)alkylsilyl, the removal of this protective group can also be carried out in the presence of tetra(lower)alkylammonium fluoride (e.g. tetrabutylammonium fluoride, etc.).

The present process includes within the scope thereof a case that the carboxy- and/or amino-protective group(s) on $R^1$ and/or $R^4$, and/or imino-protective group of $R^5$ are removed at the same time during the reaction.

The object compounds (I), (I-b), (I-d), (I-f), (I-g) and (I-h) obtained according to the Processes 1 to 7, can be isolated and purified in a conventional manner, for example, extraction, precipitation, fractional crystallization, recrystallization, chromatography, and the like.

(5) Process 5:

The compound (I) or salts thereof can be prepared by cyclizing the compound (IV) or salts thereof.

Suitable salts of the compound (IV) may be the same as those for the compound (I).

This reaction is preferably carried out by heating the compound (IV) in a conventional solvent which does not adversely influence the reaction such as dioxane, hexamethylphosphoramide, benzene, toluene, xylene, dimethyl sulfoxide, N,N-dimethylformamide, pyridine, etc., or a mixture thereof.

This reaction can also be carried out in the presence of hydroquinone.

The reaction temperature of this reaction is not critical and the reaction is usually carried out under from warming to heating.

(6) Process 6:

The compound (I-g) or salts thereof can be prepared by reacting the compound (V) or salts thereof with a halogenating agent.

Suitable salts of the compounds (I-g) and (V) may be acid addition salts such as those given for the compound (I).

Suitable examples of the halogenating agent to be used in this process may include a conventional one which is capable of transforming a hydroxy group to halogen such as phosphorus oxyhalide [e.g. phosphorus oxybromide, phosphorus oxychloride, etc.], phosphorus pentahalide [e.g. phosphorus pentabromide, phosphorus pentachloride, phosphorus pentafluoride, etc.], phosphorus trihalide [e.g. phosphorus tribromide, phosphorus trichloride, phosphorus trifluoride, etc.], thionyl halide [e.g. thionyl chloride, thionyl bromide, etc.], triphenylphosphine dihalide [e.g. triphenylphosphine dichloride, triphenylphosphine dibromide, etc.] a combination of triphenylphosphine and carbon tetrahalide [e.g. carbon tetrachloride, etc.], or the like.

This reaction is usually carried out in a conventional solvent which does not adversely influence the reaction such as methylene chloride, chloroform, carbon tetrachloride, benzene, tetrahydrofuran, dimethylformamide, dimethyl sulfoxide, etc., or a mixture thereof. In case that the halogenating agent is liquid, it can be used as a solvent.

The reaction temperature is not critical, and the reaction can be carried out under cooling to heating.

(7) Process 7:

The compound (I-h) or salts thereof can be prepared by reacting the compound (I-d) or salts thereof with the compound (XI) or salts thereof.

Suitable salts of the compound (I-h) may be the same as those for the compound (I).

Suitable salts of the compound (XI) may be the same acid addition salts as exemplified for the compound (I).

This reaction is usually carried out in a conventional solvent which does not adversely influence the reaction such as tetrahydrofuran, dioxane, water, methanol, ethanol, buffer solution (e.g. phosphate buffer, etc.), etc., or a mixture thereof.

This reaction can be carried out in the presence of an organic or inorganic base such as those given in the explanation of Process 2.

The reaction temperature is not critical, and the reaction is usually carried out under from cooling to warming.

Methods A to E for preparing the new starting compounds (III) and (IV) or salts thereof are explained in detail in the following.

(A) Method A

The compound (III-a) or salts thereof can be prepared by reacting the compound (VI) or a reactive derivative at the hydroxy group thereof or salts thereof with the compound (XII) or salts thereof.

Suitable salts of the compounds (III-a), (VI) and (XII) may be the same as those for the compound (III).

Suitable reactive derivative at the hydroxy group of the compound (VI) may include a conventional one such as halide (e.g. chloride, bromide, iodide, etc.), sulfonate e.g. methanesulfonate, benzenesulfonate, toluenesulfonate, etc.), and the like, in which more preferable example may be sulfonate.

The starting compound (VI) or a reactive derivative at the hydroxy group thereof of this method is new and can be prepared by the methods described in the Preparations mentioned below, or by a conventional process.

Preferable example of the compound (XII) may be ar(lower)alkanethiol such as mono- or di- or triphenyl(lower)alkanethiol (e.g. phenylmethanethiyl, diphenylmethanethiol, triphenylmethanethiol, etc.), thio(lower-)alkanoic S-acid (e.g. thioacetic S-acid, etc.), thioarenoic S-acid (e.g. thiobenzoic S-acid, etc.), and the like, in which more preferable example may be triphenyl($C_1$–$C_4$)alkanethiol, thio($C_1$–$C_4$)alkanoic S-acid and thio ($C_6$–$C_{10}$)arenoic S-acid, and the most preferable one may be thioacetic S-acid.

In case that the compound (XII) may be ar(lower)alkanethiol or thio(lower)alkanoic S-acid, the starting compound (VI) of the present reaction is preferably used in a form of its reactive derivative at the hydroxy group, and in such a case, this reaction is usually carried out in the presence of an organic or inorganic base such as those exemplified in the explanation of Process 1.

In case that suitable example of compound (XII) may be thio(lower)alkanoic S-acid or thioarenoic S-acid, this reaction is preferably carried out in the presence of a conventional condensing agent such as combination of triarylphosphine (e.g. triphenylphosphine, etc.) and di(lower)alkyl azodicarboxylate (e.g. diethyl azodicarboxylate, etc.).

This reaction is usually carried out in a conventional solvent which does not adversely influence the reaction such as dichloromethane, methanol, ethanol, propanol, pyridine, N,N-dimethylformamide, 4-methyl-2-pentanone, tetrahydrofuran, etc., or a mixture thereof.

The reaction temperature is not critical and the reaction is usually carried out under from cooling to warming.

In this method, the configuration of the carbon atom substituted with the hydroxy group of the compound (VI) is inverted in the compound (III-a).

(B) Method B

The compound (III) or salts thereof can be prepared by subjecting the compound (III-a) or salts thereof to removal reaction of the mercapto-protective group.

Suitable salts of the compound (III-a) may be the same as those for the compound (III).

This removal reaction can be carried out by a conventional method as described below, which can be selected according to the kind of mercapto-protective group to be removed.

In case that the protective groups may be ar(lower)alkyl group, it can generally be removed by treating, for example, with a silver compound (e.g. silver nitrate, silver carbonate, etc.), or reacting with a mercapto compound (e.g. 2-mercaptoethanol, etc.) in the presence of an acid (e.g. trifluoroacetic acid, etc.).

The reaction with the silver compound as stated above is preferably carried out in the presence of an organic base (e.g. pyridine, etc.).

The resultant silver salt of compound (III) can be transformed into its alkalimetal salt, if necessary, by reacting with alkali metal halide (e.g. sodium iodide, potassium iodide, etc.).

Further, in case that the protective groups may be acyl group, it can generally be removed by solvolysis such as hydrolysis using an acid or base, alcoholysis using a base, and the like.

Suitable acid or base used in these reactions may be the same such as those given in the explanation of hydrolysis of the Process 2.

The reaction is usually carried out in a conventional solvent which does not adversely influence the reaction such as water, alcohol (e.g. methanol, ethanol, propanol, allyl alcohol, etc.), pyridine, N,N-dimethylformamide, etc., or a mixture thereof, and further in case that the base or acid to be used is in liquid, it can also be used as a solvent.

The alcoholysis is usually carried out in a conventional alcohol such as methanol, ethanol, propanol, allyl alcohol, and the like.

The reaction temperature is not critical and the reaction is usually carried out under from cooling to warming.

(C) Method C:

The compound (VIII) or salts thereof can be prepared by reacting the compound (VII) or salts thereof with compound (III).

Suitable salts of the compound (VIII) may be the same as those for the compound (I).

This reaction can be carried out in the presence of a base as exemplified for the explanation of Process 1.

This reaction is usually carried out in a conventional solvent which does not adversely influence the reaction such as water, dichloromethane, acetonitrile, alcohol (e.g. methanol, ethanol, etc.), tetrahydrofuran, dioxane, acetone, etc., or a mixture thereof.

The reaction temperature is not critical and the reaction is usually carried out under from cooling to heating.

(D) Method D:

The compound (IX) or salts thereof can be prepared by reacting the compound (VIII) or salts thereof with the compound (XIII) or salts thereof.

Suitable salts of the compound (IX) may be the same as those for the compound (I).

Suitable salts of the compound (XIII) may be salts with bases such as those given for the compound (I).

Suitable example of the compound (XIII) may be oxalyl halide, in which the carboxy group may be protected by a conventional carboxy-protective group as mentioned above.

This reaction can be carried out in the presence of a base as mentioned in Process 2.

This reaction is usually carried out in a conventional solvent which does not adversely influence the reaction such as dioxane, acetonitrile, chloroform, dichloromethane, hexamethylphosphoramide, dichloroethane, tetrahydrofuran, ethyl acetate, dimethyl sulfoxide, N,N-dimethylformamide, pyridine, etc., or a mixture thereof.

The reaction temperature of this reaction is not critical and the reaction is usually carried out under from cooling to warming.

(E) Method E:

The compound (IV) or salts thereof can be prepared by reacting the compound (IX) or salts thereof with the compound (X).

This reaction is usually carried out in a conventional solvent which does not adversely influence the reaction such as dioxane, acetonitrile, chloroform, dichloromethane, hexamethylphosphoramide, dichloroethane, tetrahydrofuran, ethyl acetate, dimethyl sulfoxide, N,N-dimethylformamide, pyridine, benzene, toluene, xylene, etc., or a mixture thereof.

The reaction temperature of this reaction is not critical and the reaction is usually carried out under from warming to heating.

The object compound (I) and pharmaceutically acceptable salts thereof of the present invention are novel and exhibit high antimicrobial activity, inhibiting the growth of a wide variety of pathogenic microorganisms including Gram-positive and Gram-negative microorganisms and are useful as antimicrobial agents.

In the present invention, the object compound (I) possessing more potent antimicrobial activity can be represented by the following formula:

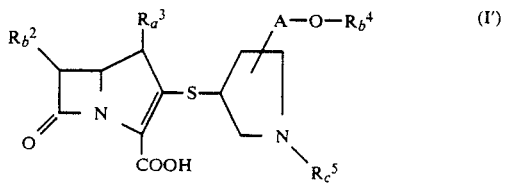

in which $R_b^2$ and A are each as defined above, $R_a^3$ is lower alkyl, $R_a^4$ is monohalo(lower)alkyl, mono- or di(lower)alkylamino(lower)alkyl, mono-or di(lower)alkylcarbamoyl(lower)alkyl, or carboxy(lower)alkyl, and $R_c^5$ is hydrogen, lower alkanimidoyl or lower cycloalkenyl which may have suitable substituent(s), and pharmaceutically acceptable salts thereof.

Particularly, the compound (I) possessing the most potent antimicrobial activity can be represented by the following formula:

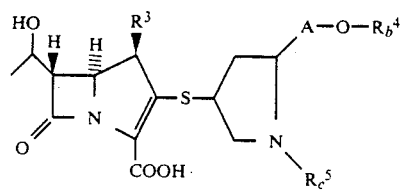

in which $R^3$, $R_b^4$, $R_c^5$ and A are each as defined above, and pharmaceutically acceptable salts thereof.

Now in order to show the utility of the object compound (I), the test data on antimicrobial activity of the representative compound of the compound (I) of this invention is shown in the following.

in vitro Antimicrobial Activity

Test Method:

in vitro Antimicrobial Activity was determined by the two-fold agar-plate dilution method as described blow.

One loopful of an overnight culture of a test strain in Trypticase-soy broth ($10^6$ viable cells per ml) was streaked on heart infusion agar (HI-agar) containing graded concentrations of the test compound, and the minimal inhibitory concentration (MIC) was expressed in terms of mg/ml after incubation at 37° C. for 20 hours.

Test Compound:
The product of Example (2-1).
Test Result:

| Test Strain | MIC ($\mu$g/ml) |
|---|---|
| P. aeruginosa 26 | 0.39 |

For therapeutic administration, the object compound (I) and the pharmaceutically acceptable salts thereof of the present invention are used in the form of conventional pharmaceutical preparation which contains said compound, as an active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade, and the like.

If needed, there may be included in the above preparations auxiliary substances, stabilizing agents, wetting agents and other commonly used additives such as lactose, stearic acid, magnesium stearate, terra alba, sucrose, corn starch, talc, gelatin, agar, pectin, peanut oil, olive oil, cacao butter, ethylene glycol, tartaric acid, citric acid, fumaric acid, and the like.

While the dosage of the compound (I) may vary from and also depend upon the age, conditions of the patient, a kind of diseases, a kind of the compound (I) to be applied, etc. In general, amount between 1 mg and about 4,000 mg or even more per day may be administered to a patient. An average single dose of about 1 mg, 10 mg, 50 mg, 100 mg, 250 mg, 500 mg, 1000 mg, 2000 mg, of the object compound (I) of the present invention may be used in treating diseases infected by pathogenic microorganisms.

The following Preparations and Examples are given for the purpose of illustrating this invention in more detail.

Preparation 1

A mixture of (2S,4R)-4-t-butyldimethylsilyloxy-2-hydroxymethyl-1-(4-nitrobenzyloxycarbonyl)pyrrolidine (10.0 g), methanol (100 ml) and 20% palladium hydroxide on carbon (0.5 g) was stirred under atmospheric pressure of hydrogen at ambient temperature for 3 hours. The catalyst was filtered off and the filtrate was concentrated under reduced pressure to give a syrup. To a solution of the syrup in a mixture of tetrahydrofuran (100 ml) and water (100 ml) was dropwise added a solution of chloroacetyl chloride (5.0 ml) in tetrahydrofuran (10 ml) under ice-cooling with stirring, keeping the pH between 8-9 with 4N aqueous sodium hydroxide. The mixture was stirred at the same condition for 2 hours and extracted with a mixture of ethyl acetate and tetrahydrofuran (1:1 V/V) (100 ml×5). The solution was dried over magnesium sulfate and concentrated under reduced pressure to give a syrup. The syrup was subjected to a column chromatography on silica gel (200 g) and eluted with a mixture of methanol and dichloromethane (1:99 V/V) to give (2S,4R)-4-t-butyldimethylsilyloxy-1-chloroacetyl-2-(hydroxymethyl)pyrrolidine (4.22 g).

IR (Neat): 3400, 1660–1630 cm$^{-1}$

NMR (CDCl$_3$, $\delta$): 1.10 (6H, s), 1.90 (9H, s), 1.5–2.3 (3H, m), 3.3–3.9 (5H, m), 4.03 (2H, s), 4.1–4.5 (3H, m)

PREPARATION 2

A solution of (2S,4R)-4-t-butyldimethylsilyloxy-1-chloroacetyl-2-(hydroxymethyl)pyrrolidine (4.20 g) in tetrahydrofuran (20 ml) was dropwise added to a suspension of sodium hydride (62.8% in oil suspension) (0.55 g) in tetrahydrofuran (60 ml) at 20°–30° C. and the mixture was stirred at 25°–30° C. for 3 hours. The mixture was concentrated under reduced pressure to give a syrup. A solution of the syrup in ethyl acetate (80 ml) was washed with water (100 ml), dried over magnesium sulfate and concentrated under reduced pressure to give a residue. The residue was subjected to a column chromatography on silica gel (30 g) and eluted with a mixture of methanol and chloroform (1:99 V/V) to give (6S,8R)-8-t-butyl-dimethylsilyloxy-2-oxo-1-aza-4-oxabicyclo[4.3.0]nonane (3.49 g).

mp 81°–82° C.

IR (Nujol): 1650 cm$^{-1}$

NMR (CDCl$_3$, $\delta$): 1.10 (6H, s), 1.90 (9H, s), 1.3–1.6 (1H, m), 1.8–2.1 (1H, m), 3.1–3.5 (2H, m), 3.8–4.3 (5H, m), 4.4–4.6 (1H, m)

MS: 256 (M$^+$-15), 214

PREPARATION 3

A suspension of (6S,8R)-8-t-butyldimethylsilyloxy-2-oxo-1-aza-4-oxabicyclo[4.3.0]nonane (1.43 g) in 6N hydrochloric acid (14 ml) was heated for 3 hours under reflux. After cooling, the solution was washed with ethyl acetate (7 ml×2) and concentrated under reduced pressure to give (2S,4R)-2-(carboxymethyloxymethyl)-4-hydroxypyrrolidine hydrochloride.

PREPARATION 4

To a solution of the compound obtained in Preparation 3 in a mixture of water (30 ml) and tetrahydrofuran (30 ml) was dropwise added a solution of 4-nitrobenzyloxycarbonyl chloride (1.36 g) in tetrahydrofuran (6 ml) under ice-cooling with stirring, keeping the pH between 8-9 with 4N aqueous sodium hydroxide. The mixture was stirred under the same condition for 2 hours, adjusted to pH 2.5 with 6N hydrochloric acid and extracted with ethyl acetate (50 ml×2). The organic solution was combined, washed with brine, dried over magnesium sulfate and concentrated under reduced pressure to give a syrup. The syrup was subjected to a column chromatography on silica gel (20 g) and eluted with a mixture of methanol and chloroform (3:97 V/V) to give (2S,4R)-2-(carboxy-methyloxymethyl)-4-hydroxy-1-(4-nitrobenzyloxycarbonyl)pyrrolidine (1.45 g).

IR (Neat): 3600–3300, 1750–1680 cm$^{-1}$

NMR (DMSO-d$_6$, $\delta$): 1.8–2.2 (2H, m), 3.2–3.7 (4H, m), 3.98 (2H, s), 3.9–4.4 (2H, m), 5.20 (2H, s), 7.58 (2H, d, J=8.5 Hz), 8.18 (2H, d, J=8.5 Hz)

PREPARATION 5

A solution of methanesulfonyl chloride (0.62 ml) in dichloromethane (2 ml) was dropwise added to a solution of (2S,4R)-2-(carboxymethyloxymethyl)-4-hydroxy-1-(4-nitrobenzyloxycarbonyl)pyrrolidine (1.42 g) and triethylamine (1.4 ml) in dichloromethane (14 ml) at 0°–5° C., and the mixture was stirred at the same temperature for 1 hour. The mixture was poured into water (50 ml), adjusted to pH 2.5 with 6N hydrochloric acid and extracted with dichloromethane (50 ml×2). The organic layer was washed with brine, dried over magnesium sulfate and concentrated under reduced pressure to give a syrup. The syrup was subjected to a column chromatography on silica gel (20 g) and eluted with a mixture of methanol and chloroform (1:99 V/V) to give (2S,4R)-2-(carboxymethyloxymethyl)-4-methanesulfonyl-oxy-1-(4-nitrobenzyloxycarbonyl)pyrrolidine (1.30 g).

IR (CHCl$_3$): 1750, 1705 cm$^{-1}$

NMR (CDCl$_3$, δ): 2.3–2.5 (2H, m), 3.03 (3H, s), 3.5–4.4 (5H, m), 4.08 (2H, s), 5.22 (2H, s), 5.2–5.4 (1H, m), 5.8–6.2 (1H, m), 7.48 (2H, d, J=8.5 Hz), 8.19 (2H, d, J=8.5 Hz)

PREPARATION 6

A solution of isobutyl chloroformate (1.08 ml) in tetrahydrofuran (3 ml) was dropwise added to a solution of (2S,4R)-2-(carboxymethyloxymethyl)-4-methanesulfonyloxy-1-(4-nitrobenzyloxycarbonyl)pyrrolidine (2.4 g) and triethylamine (1.55 ml) in tetrahydrofuran (50 ml) at −10°∼5° C., and the mixture was stirred at the same temperature for 0.5 hour. The precipitate was filtered off. To the filtrate was added sodium borohydride (0.7 g) and water (30 ml) at 0° C. After 1 hour, glacial acetic acid (3 ml) was added to the mixture. The mixture was poured into a mixture of water (50 ml) and ethyl acetate (50 ml). The organic layer was separated, washed with water, saturated aqueous sodium hydrogen carbonate and brine in turn, dried over magnesium sulfate, and concentrated under reduced pressure to give a syrup. The syrup was subjected to a column chromatography on silica gel (30 g) and eluted with a mixture of methanol and chloroform (5:95 V/V) to give (2S,4R)-2-(2-hydroxyethyloxymethyl)-4-methanesulfonyloxy-1-(4-nitrobenzyloxycarbonyl)pyrrolidine (2.10 g).

IR (CH$_2$Cl$_2$): 3460, 1680–1720, 1605 cm$^{-1}$

NMR (CDCl$_3$, δ): 2.1–2.5 (2H, m), 3.02 (3H, s), 3.4–4.0 (8H, m), 4.1–4.4 (1H, m), 5.2–5.5 (3H, m), 7.53 (2H, d, J=8.5 Hz), 8.27 (2H, d, J=8.5 Hz)

PREPARATION 7

To a solution of (2S,4R)-2-(2-hydroxyethyloxymethyl)-4-methanesulfonyloxy-1-(4-nitrobenzyloxycarbonyl)pyrrolidine (5.05 g) in dichloromethane (30 ml) was added hexafluoropropene-diethylamine complex (2.65 ml) at 0°–5° C., and the mixture was stirred at the same temperature for 3 hours and at ambient temperature for 18 hours. The mixture was poured into ice-water (30 ml). The organic layer was separated, dried over magnesium sulfate and concentrated under reduced pressure to give a syrup. The syrup was subjected to a column chromatography on silica gel (80 g) and eluted with chloroform to give (2S,4R)-2-(2-fluoroethyloxymethyl)-4-methanesulfonyloxy-1-(4-nitrobenzyloxycarbonyl)pyrrolidine (5.05 g).

IR (Neat): 1720–1665 cm$^{-1}$

NMR (CDCl$_3$, δ): 3.02 (3H, s), 5.22 (2H, s)

PREPARATION 8-1

To a mixture of dimethylformamide (3.9 ml) and tetrahydrofuran (30 ml) was dropwise added phosphorus oxychloride (3.75 ml) at 0°–10° C. and the mixture was stirred at the same temperature for 30 minutes. To the mixture was added a solution of (2S,4R)-2-(carboxymethyloxymethyl)-4-methanesulfonyloxy-1-(4-nitrobenzyloxycarbonyl)pyrrolidine (14.50 g) in tetrahydrofuran (15 ml) at 0°–10° C. and the mixture was stirred at the same temperature for 30 minutes. The resulting mixture was dropwise added to a mixture of dimethylamine hydrochloride (50 g) and triethylamine (100 ml) in methanol (200 ml) at 0°–10° C. with stirring. The mixture was stirred at the same temperature for 2 hours. The insoluble material was filtered off and the filtrate was concentrated under reduced pressure to give a syrup. The syrup was dissolved in ethyl acetate (200 ml), washed with water (200 ml), 1N hydrochloric acid (200 ml), saturated aqueous sodium hydrogen carbonate (200 ml) and brine (200 ml), in turn, dried over magnesium sulfate, and concentrated under reduced pressure to give (2S,4R)-2-(dimethylcarbamoyl)methyloxymethyl-4-methanesulfonyloxy-1-(4-nitrobenzyloxycarbonyl)pyrrolidine (12.03 g).

IR (Neat): 1705, 1655 cm$^{-1}$

NMR (CDCl$_3$, δ): 2.90 (6H, s), 3.01 (3H, s), 4.10 (2H, s)

PREPARATION 8-2

(2S,4R)-4-Methanesulfonyloxy-2-(methylcarbamoyl)methyloxymethyl-1-(4-nitrobenzyloxycarbonyl)pyrrolidine (13.99 g) was obtained by reacting (2S,4R)-2-(carboxymethyloxymethyl)-4-methanesulfonyloxy-1-(4-nitrobenzyloxycarbonyl)pyrrolidine (14.20 g) successively with dimethylformamide-phosphorus oxychloride complex and a 30% solution (100 ml) of methylamine in methanol in substantially the same manner as that of Preparation 8-1).

IR (Neat): 1710–1655 cm$^{-1}$

NMR (CDCl$_3$, δ): 2.78 (3H, d, J=6 Hz), 3.03 (3H, s), 3.93 (2H, s)

PREPARATION 9

To a suspension of sodium borohydride (1.85 g) in tetrahydrofuran (75 ml) was added boron trifluoride etherate (18.5 ml) in a nitrogen stream with stirring at 0°–10° C. The mixture was stirred at the same temperature for 30 minutes. To the mixture was added a solution of (2S,4R)-2-(dimethylcarbamoyl)methyloxy-methyl-4-methanesulfonyloxy-1-(4-nitrobenzyloxycarbonyl)pyrrolidine (7.50 g) in tetrahydrofuran (7.5 ml) at 0°–10° C. The mixture was stirred at the same temperature for 3 hours and at ambient temperature overnight. Methanol (5 ml) was added to the reaction mixture at 0°–10° C. After 2 hours, insoluble material was filtered off and the filtrate was concentrated under reduced pressure to give a residue. A solution of the residue in a mixture of concentrated hydrochloric acid (7 ml) and methanol (70 ml) was stirred at ambient temperature overnight. The mixture was concentrated under reduced pressure to give a syrup. The syrup was dissolved in ethyl acetate (75 ml), washed with water (75 ml×2), saturated aqueous sodium hydrogen carbonate (75 ml×2) and brine (75 ml), in turn, dried over magnesium sulfate, and concentrated under reduced pressure to give a syrup. The syrup was subjected to a column chromatography on silica gel (100 g) and eluted with a mixture of methanol and chloroform (5:95 and then, 10:90 V/V) to give (2S,4R)-2-[2-(dimethylamino)ethyloxymethyl]-4-methanesulfonyloxy-1-(4-nitrobenzyloxycarbonyl)pyrrolidine (6.83 g).

IR (Neat): 1705 cm$^{-1}$
NMR (CDCl$_3$, δ): 2.30 (6H, s), 3.00 (3H, s)

PREPARATION 10

To a suspension of sodium borohydride (1.87 g) in tetrahydrofuran (75 ml) was added boron trifluoride etherate (18.7 ml) in a nitrogen stream with stirring at 0°-10° C. The mixture was stirred at the same temperature for 30 minutes. To the mixture was added a solution of (2S,4R)-4-methanesulfonyloxy-2-(methylcarbamoyl)methyloxymethyl-1-(4-nitrobenzyloxycarbonyl)pyrrolidine (7.35 g) in tetrahydrofuran (7.5 ml) at 0°-10° C. The mixture was stirred at the same temperature for 3 hours and at ambient temperature overnight. Methanol (5 ml) was added to the reaction mixture at 0°-10° C. After 2 hours, insoluble material was filtered off and the filtrate was concentrated under reduced pressure to give a residue. A solution of the residue in a mixture of concentrated hydrochloric acid (7 ml) and methanol (70 ml) was stirred at ambient temperature overnight. The mixture was concentrated under reduced pressure to give a syrup. The syrup was dissolved in ethyl acetate (75 ml), washed with water (75 ml×2) and brine (75 ml) in turn, dried over magnesium sulfate, and concentrated under reduced pressure to give a syrup. The syrup was dissolved in a mixture of water (30 ml) and tetrahydrofuran (30 ml), and to this mixture was added a solution of 4-nitrobenzyloxycarbonyl chloride (3.55 g) in tetrahydrofuran (7 ml) under ice-cooling with stirring, keeping the pH between 8.5-9.5 with 4N aqueous sodium hydroxide. The mixture was stirred at the same condition for 2 hours. The tetrahydrofuran was removed under reduced pressure from the reaction mixture and ethyl acetate (50 ml) was added thereto. The organic layer was separated, dried over magnesium sulfate and concentrated under reduced pressure to give a syrup. The syrup was subjected to a column chromatography on silica gel (100 g) and eluted with a mixture of methanol and chloroform (1:99 V/V) to give (2S,4R)-4-methanesulfonyloxy-2-[2-{N-methyl-N-(4-nitrobenzyloxycarbonyl)amino}ethyloxymethyl]-1-(4-nitrobenzyloxycarbonyl)pyrrolidine (8.33 g).

IR (Neat): 1710-1690 cm$^{-1}$
NMR (CDCl$_3$, δ): 2.95 (3H, s), 3.01 (3H, s)

PREPARATION 11

A solution of (2S,4R)-2-(carboxymethyloxymethyl)-4-methanesulfonyloxy-1-(4-nitrobenzyloxycarbonyl)-pyrrolidine (5.20 g) in allyl alcohol (52 ml) was refluxed in the presence of sulfuric acid (0.5 ml) for 5 hours. After cooling, triethylamine (3.14 ml) was added to the mixture. The mixture was concentrated under reduced pressure to give a syrup. The syrup was dissolved in ethyl acetate (100 ml), washed in turn with water (100 ml) and brine (100 ml), dried over magnesium sulfate, and concentrated under reduced pressure to give (2S,4R)-2-(allyloxycarbonylmethyloxymethyl)-4-methanesulfonyloxy-1-(4-nitrobenzyloxycarbonyl)pyrrolidine (6.05 g).

IR (Neat): 1750, 1705 cm$^{-1}$
NMR (CDCl$_3$, δ): 3.00 (3H, s), 4.05 (2H, s)

PREPARATION 12-1

A solution of (2S,4R)-2-(2-fluoroethyloxymethyl)-4-methanesulfonyloxy-1-(4-nitrobenzyloxycarbonyl)pyrrolidine (4.95 g) in dimethylformamide (5 ml) was added to a mixture of thioacetic S-acid (1.26 ml) and potassium tert-butoxide (1.98 g) in dimethylformamide (25 ml) in a nitrogen stream, and the mixture was heated at 75°-80° C. for 2 hours. The mixture was poured into ice-water (100 ml) and extracted with ethyl acetate (100 ml). The extract was washed with water (100 ml×2) and brine (100 ml), in turn, dried over magnesium sulfate, and concentrated under reduced pressure to give a syrup. The syrup was subjected to a column chromatography on silica gel (80 g) and eluted with chloroform to give (2S,4S)-4-acetylthio-2-(2-fluoroethyloxymethyl)-1-(4-nitrobenzyloxycarbonyl)pyrrolidine (1.75 g).

IR (Neat): 1710-1700 cm$^{-1}$
NMR (CDCl$_3$, δ): 2.31 (3H, s), 5.20 (2H, s)

The following compounds were obtained in substantially the same manner as that of Preparation 12-1).

PREPARATION 12-2

(2S,4S)-4-Acetylthio-2-(dimethylcarbamoyl)methyloxymethyl-1-(4-nitrobenzyloxycarbonyl)pyrrolidine IR (Neat): 1700, 1655 cm$^{-1}$
NMR (CDCl$_3$, δ): 2.31 (3H, s), 2.93 (6H, s), 4.10 (2H, s)

PREPARATION 12-3

(2S,4S)-4-Acetylthio-2-(methylcarbamoyl)methyloxymethyl-1-(4-nitrobenzyloxycarbonyl)pyrrolidine IR (Neat): 1710-1665 cm$^-$
NMR (CDCl$_3$, δ): 2.33 (3H, s), 2.80 (3H, d, J=6 Hz), 3.94 (2H, s)

PREPARATION 12-4

(2S,4S)-4-Acetylthio-2-[2-(dimethylamino)ethyloxymethyl]-1-(4-nitrobenzyloxycarbonyl)pyrrolidine IR (Neat): 1710-1690 cm$^{-1}$
NMR (CDCl$_3$, δ): 2.27 (6H, s), 2.31 (3H, s)

PREPARATION 12-5

(2S,4S)-4-Acetylthio-2-[2-{N-methyl-N-(4-nitrobenzyloxycarbonyl)amino}ethyloxymethyl]-1-(4-nitrobenzyloxycarbonyl)pyrrolidine IR (Neat): 1710-1685 cm$^{-1}$
NMR (CDCl$_3$, δ): 2.30 (3H, s), 2.97 (3H, s)

PREPARATION 12-6

(2S,4S)-4-Acetylthio-2-(allyloxycarbonylmethyloxymethyl)-1-(4-nitrobenzyloxycarbonyl)pyrrolidine IR (Neat): 1755, 1710-1695 cm$^{-1}$
NMR (CDCl$_3$, δ): 2.32 (3H, s), 4.15 (2H, s)

PREPARATION 13-1

To a solution of (2S,4S)-4-acetylthio-2-(2-fluoroethyloxymethyl)-1-(4-nitrobenzyloxycarbonyl)pyrrolidine (1.70 g) in methanol (35 ml) was dropwise added a 28% solution (1.2 ml) of sodium methoxide in methanol at −10°~−5° C. in a nitrogen stream, followed by stirring at the same temperature for 1 hour. To the mixture was added acetic acid (0.4 ml) at −10°~−5° C. The mixture was concentrated under reduced pressure to give a residue. The residue was poured into a mixture of water (50 ml) and ethyl acetate (50 ml). The organic layer was separated, dried over magnesium sulfate and concentrated under reduced pressure to give a syrup. The syrup was subjected to a column chromatography on silica gel (25 g) and eluted with chloroform to give (2S,4S)-2-(2-fluoroethyloxymethyl)-4-mercapto-1-(4-nitrobenzyloxycarbonyl)pyrrolidine (0.91 g).
IR (Neat): 1710–1685 cm$^{-1}$
NMR (CDCl$_3$,δ): 5.18 (2H, s)
MS: 358 (M+, 324, 281

The following compounds were obtained in substantially the same manner as that of Preparation 13-1.

PREPARATION 13-2

(2S,4S)-2-(Dimethylcarbamoyl)methyloxymethyl-4-mercapto-1-(4-nitrobenzyloxycarbonyl)pyrrolidine
IR (Neat): 1700, 1650 cm$^{-1}$
NMR (CDCl$_3$, δ): 2.93 (6H, s), 4.11 (2H, s)

PREPARATION 13-3

(2S,4S)-4-Mercapto-2-(methylcarbamoyl)methyloxymethyl-(4-nitrobenzyloxycarbonyl)pyrrolidine
IR (Neat): 1710–1660 cm$^{-1}$
NMR (CDCl$_3$,δ): 2.79 (3H, d, J=6 Hz), 3.96 (2H, s)

PREPARATION 13-4

(2S,4S)-2-[2-(Dimethylamino)ethyloxymethyl]-4-mercapto-1-(4-nitrobenzyloxycarbonyl)pyrrolidine
IR (Neat): 1710–1690 cm$^{-1}$
NMR (CDCl$_3$,δ): 2.50 (6H, s)

PREPARATION 13-5

(2S,4S)-4-Mercapto-2-[2-(N-methyl-N-(4-nitrobenzyloxycarbonyl)amino) ethyloxymethyl]-1-(4-nitrobenzyloxycarbonyl)pyrrolidine
IR (Neat): 1710–1690 cm$^{-1}$
NMR (CDCl$_3$, δ): 2.98 (3H, s)

PREPARATION 13-6

To a solution of (2S,4S)-4-acetylthio- 2-(allyloxycarbonylmethyloxymethyl)-1-(4-nitrobenzyloxycarbonyl)pyrrolidine (4.25 g) in allyl alcohol (40 ml) was added sodium hydride (62.8% in oil suspension) (0.5 g) at −5°~0° C. in a nitrogen stream. After stirring for 1 hour, acetic acid (1 ml) was added to the mixture. The mixture was concentrated under reduced pressure to give a syrup. The syrup was dissolved in ethyl acetate (50 ml), washed in turn with water (50 ml) and brine (50 ml), dried over magnesium sulfate, and concentrated under reduced pressure to give a syrup. The syrup was subjected to a column chromatography on silica gel (30 g) and eluted with chloroform to give (2S,4S)-2-(allyloxycarbonylmethyloxymethyl)-4-mercapto-1-(4-nitrobenzyloxycarbonyl)pyrrolidine (2.29 g).
IR (Neat): 1750, 1705 cm$^{-1}$
NMR (CDCl$_3$,δ): 4.07 (2H, s)

PREPARATION 14

(2S,4R)-1-Benzyloxycarbonyl-2-(2-hydroxyethyloxymethyl)-4-methanesulfonyloxypyrrolidine was obtained in 89.0% yield in substantially the same manner as that of Preparation 6.
IR (Neat): 3550–3350, 1715–1630 cm$^{-1}$
NMR (CDCl$_3$,δ): 2.2–2.5 (2H, m), 2.95 (3H, s), 3.4–4.3 (10H, m), 5.12 (2H, s), 5.2–5.3 (1H, m), 7.31 (5H, s)

PREPARATION 15

To a solution of (2S,4R)-1-benzyloxycarbonyl-2-(2-hydroxyethyloxymethyl)-4-methanesulfonyloxypyrrolidine (188 g) in dichloromethane (564 ml) was dropwise added a solution of hexafluoropropene diethylamine complex (115 ml) in dichloromethane (115 ml) at −10°~0° C. for 30 minutes. The solution was stirred at ambient temperature for 2 35 hours and at 30°~35° C. for 10 hours, and then poured into a mixture of water (600 ml) and dichloromethane (400 ml). The organic layer was washed with saturated sodium hydrogen carbonate (800 ml×3) and concentrated under reduced pressure to give a syrup. The syrup was dissolved in methanol (600 ml). To the solution was added a 28% solution (30 ml) of sodium methoxide in methanol and the mixture was stirred at ambient temperature for one hour. To the mixture was added glacial acetic acid (10 ml) and concentrated under reduced pressure to give a residue. The residue was suspended in dichloromethane (800 ml), washed with water (400 ml), dried over magnesium sulfate and concentrated under reduced pressure to give a syrup. The syrup was subjected to a column chromatography on silica gel (1 kg) and eluted with a mixture of hexane and ethyl acetate (1:1 V/V) to give (2S,4R)-1-benzyloxycarbonyl-2-(2-fluoroethyloxymethyl)-4-methanesulfonyloxypyrrolidine (151.28 g).
IR (Neat): 1710–1685 cm$^{-1}$
NMR (CDCl$_3$,δ): 2.3–2.5 (2H, m), 2.96 (3H, s), 3.4–4.9 (9H, m), 5.20 (2H, s), 5.25–5.4 (1H, m), 7.38 (5H, m)

PREPARATION 16

A solution of (2S,4R)-1-benzyloxycarbonyl-2-(2-fluoroethyloxymethyl)-4-methanesulfonyloxypyrrolidine (8.37 g) in a mixture of concentrated hydrochloric acid (4.3 ml) and methanol (86 ml) was hydrogenated under atmospheric pressure of hydrogen at ambient temperature for 3 hours in the presence of 10% palladium on carbon (0.86 g). The catalyst was filtered off and the filtrate was concentrated under reduced pressure to give a syrup. The syrup was dissolved in a mixture of water (50 ml) and tetrahydrofuran (50 ml). To the solution was dropwise added a solution of allyl chloroformate (2.87 ml) in tetrahydrofuran (5 ml) under ice-cooling with stirring, while keeping the pH between 8 and 9 with 4N aqueous sodium hydroxide. The mixture was stirred at the same condition for one hour, extracted with ethyl acetate (100 ml), washed in turn with water (100 ml) and brine (100 ml), dried over magnesium sulfate, and concentrated under reduced pressure to give a syrup. The syrup was subjected to a column chromatography on silica gel (75 g) and eluted with a mixture of methanol and chloroform (1:99 V/V) to give (2S,4R)-1-allyloxycarbonyl-2-(2-fluoroethyloxymethyl)-4-methanesulfonyloxypyrrolidine (6.50 g).
IR (Neat): 1710–1685 cm$^{-1}$
NMR (CDCl$_3$, δ): 2.2–2.5 (2H, m), 3.00 (3H, s), 3.4–4.8 (11H, m), 5.1–5.4 (3H, m), 5.7–6.1 (1H, m)

PREPARATION 17

To a solution of (2S,4R)-1-benzyloxycarbonyl-2-{2-(2,2-dimethyl-4,6-dioxo-1,3-dioxan-5-yl)-2-oxoethyl}-oxymethyl-4-methanesulfonyloxypyrrolidine (20 g) in a mixture of acetic acid (60 ml) and methanol (60 ml) was heated under refluxing for 40 hours. The reaction mixture was poured into a mixture of ethyl acetate (400 ml) and water (400 ml). The organic layer was separated, washed with water (400 ml), saturated sodium hydrogen carbonate (400 ml), and brine (400 ml) successively, and dried over magnesium sulfate. Evaporation of the solvent gave a residue, which was chromatographed on silica gel (600 ml) eluting with 2% methanol in dichloromethane (V/V) to give (2S,4R)-1-benzyloxycarbonyl-2-[{3-(methoxycarbonyl)-2-oxopropyl}oxymethyl]-4-methanesulfonyloxypyrrolidine (15.23 g).

IR (Nujol) : 1690–1750 cm$^{-1}$

NMR (CDCl$_3$, δ): 2.25–2.50 (2H, m), 3.01 (3H, s), 3.30–4.20 (9H, m), 5.14 (2H, s), 5.20–5.35 (1H, m), 7.36 (5H, s)

PREPARATION 18

To a solution of (2S,4R)-1-benzyloxycarbonyl-2-[{3-(methoxycarbonyl)-2-oxopropyl}oxymethyl]-4-methanesulfonyloxypyrrolidine (7 g) in ethanol (80 ml) was added by portions sodium borohydride (1.2 g) at 0° C. After 6 hours, to the reaction mixture was carefully added dropwise acetone (30 ml) at 0° C. and then the solvent was evaporated in vacuo. To the resultant residue were added ethyl acetate (100 ml) and water (50 ml). The organic layer was separated, washed with brine (50 ml) and dried over magnesium sulfate. Evaporation of the solvent gave a residue, which was chromatographed on silica gel (500 ml) eluting with a mixture of dichloromethane and methanol (18:1 V/V) to give (2S,4R)-1-benzyloxycarbonyl-2-[{3-(ethoxycarbonyl)-2-hydroxypropyl}oxymethyl]-4-methanesulfonyloxypyrrolidine (5.1 g).

IR (Nujol): 3400–3500, 1685–1730 cm$^{-1}$

NMR (CDCl$_3$, δ): 1.27 (3H, t, J=7 Hz), 2.16–2.47 (4H, m), 2.97 (3H, s), 3.18–4.26 (8H, m), 4.13 (2H, q, J=7 Hz), 5.09 (2H, s), 5.12–5.20 (1H, m), 7.27 (5H, s)

PREPARATION 19

To a solution of (2S,4R)-1-benzyloxycarbonyl-2-[{3-(ethoxycarbonyl)-2-hydroxypropyl}oxymethyl]-4-methanesulfonyloxypyrrolidine (9.5 g) in acetic acid (150 ml) were added triethylamine (15 ml) and methanesulfonyl chloride (2 ml) at −40° C. and the mixture was stirred at the same temperature for 2 hours under nitrogen atmosphere. Resulting precipitate was filtered off and the filtrate was concentrated in vacuo to give a residue, which was dissolved in a mixture of ethyl acetate (100 ml) and water (50 ml). The organic layer was separated, washed with brine (50 ml) and dried over magnesium sulfate. Evaporation of the solvent gave a residue, which was chromatographed on silica gel (300 ml) eluting with a mixture of hexane and ethyl acetate (1:1 V/V) to give (2S,4R)-1-benzyloxycarbonyl-2-[{3-(ethoxycarbonyl)-2-methanesulfonyloxypropyl}oxymethyl]-4-methanesulfonyloxypyrrolidine (3.74 g).

NMR (CDCl$_3$, δ): 1.24 (3H, t, J=7 Hz), 2.27–2.40 (2H, m), 2.60–2.70 (2H, m), 2.97 (3H, s), 2.98 {3H, s), 3.44–4.23 (7H, m), 4.13 (2H, q, J=7 Hz), 5.09 (2H, s), 5.00–5.33 (2H, m), 7.27 (5H, s)

PREPARATION 20

To a solution of (2S,4R)-1-benzyloxycarbonyl-2-[{3-(ethoxycarbonyl)-2-methanesulfonyloxypropyl}oxymethyl]-4-methanesulfonyloxypyrrolidine (3.7 g) in tetrahydrofuran (40 ml) was added 1,8-diazabicyclo[5.4.0]undec-7-ene (5.1 ml) at ambient temperature and the mixture was stirred for one hour. Removal of the solvent in vacuo gave an oil which was dissolved in a mixture of ethyl acetate (100 ml), water (50 ml) and 1N-hydrochloric acid (10 ml). The organic layer was separated, washed twice with brine (50 ml) and dried over magnesium sulfate. Evaporation of the solvent gave a residue, which was chromatographed on silica gel (200 ml) eluting with a mixture of hexane and ethyl acetate (1:1 V/V) to give (2S,4R)-1-benzyloxycarbonyl-2-[{3-[ethoxycarbonyl]-2-propenyl}oxymethyl]-4-methanesulfonyloxypyrrolidine (2.72 g).

IR (Nujol): 1695–1720 cm$^{-1}$

NMR (CDCl$_3$, δ): 1.29 (3H, t, J=0.7 Hz), 2.0–2.4 (2H, m), 3.00 (3H, s), 3.47–4.25 (7H, m), 4.13 (2H, q, J=7 Hz), 5.10 (2H, s), 5.10–5.31 (1H, m), 5.74–6.04 (1H, m), 6.65–6.94 (1H, m), 7.27 (5H, s)

PREPARATION 21

Under nitrogen atmosphere at −70° C., to a solution of oxalyl chloride (4.31 ml) in dichloromethane (200 ml) were added dropwise dimethyl sulfoxide (7.01 ml), a solution of (2S,4R)-1-benzyloxycarbonyl-2-(2-hydroxyethyloxymethyl)-4-methanesulfonyloxypyrrolidine (17.57 g) in dichloromethane (50 ml) and triethylamine (37.8 ml). The reaction mixture was stirred at the same temperature for 2 hours and then allowed to warm to ambient temperature. Precipitate was filtered off and to the filtrate was added a mixture of ethyl acetate (200 ml) and water (100 ml). The organic layer was separated, washed with brine (100 ml), dried over magnesium sulfate and active carbon was added thereto. Evaporation of the solvent gave a residue, which was chromatographed on silica gel (500 ml) eluting with a mixture of dichloromethane and methanol (9:1 V/V) to give (2S,4R)-1-benzyloxycarbonyl-2-(2-oxoethyl)oxymethyl-4-methanesulfonyloxypyrrolidine (15.7 g).

IR (Nujol): 1660–1740 cm$^{-1}$

NMR (CDCl$_3$, δ): 2.05–2.45 (3H, m), 3.01 (3H, s), 3.48–4.20 (8H, m), 5.15 (2H, s), 5.20–5.40 (1H, m), 7.36 (5H, s), 9.64 (1H, br s)

PREPARATION 22

A solution of (2S,4R)-1-benzyloxycarbonyl-2-(2-oxoethyl)oxymethyl-4-methanesulfonyloxypyrrolidine (15.7 g) and ethyl 2-triphenylphosphoranylideneacetate (16.2 g) in toluene (150 ml) was heated under refluxing for 3 hours. The solvent was removed in vacuo to give a residue, which was chromatographed on silica gel (700 ml) eluting with a mixture of hexane and ethyl acetate (2:1-1:1 V/V) to give (2S,4R)-1-benzyloxycarbonyl-2-[{3-(ethoxycarbonyl)-2-propenyl}oxymethyl]-4-methanesulfonyloxypyrrolidine (12.86 g).

IR (Nujol): 1695–1720 cm$^{-1}$

NMR (CDCl$_3$, δ): 1.29 (3H, t, J=0.7 Hz), 2.0–2.4 (2H, m), 3.00 (3H, s), 3.47–4.25 (7H, m), 4.13 (2H, q, J=7 Hz), 5.10 (2H, s), 5.10–5.31 (1H, m), 5.74–6.04 (1H, m), 6.65–6.94 (1H, m), 7.27 (5H, s)

PREPARATION 23

To a solution of (2S,4R)-1-benzyloxycarbonyl-2-[{3-(ethoxycarbonyl)-2-propenyl}oxymethyl]-4-methanesulfonyloxypyrrolidine (10 g) in tetrahydrofuran (120 ml) was added dropwise 1.0 M solution of diisobutylaluminum hydride in toluene (56.6 ml) at −40° C. and the mixture was allowed to warm to 0° C. and stirred for 10 hours at the same temperature. The reaction mixture was added dropwise 1N hydrochloric acid (50 ml), and the resulting precipitate was filtered off. The filtrate was dissolved in a mixture of ethyl acetate (200 ml) and water (100 ml). The organic layer was separated, washed with brine (100 ml), dried over magnesium sulfate and treated with active carbon. Evaporation of the solvent gave a residue, which was chromatographed on silica gel (200 ml) eluting with a mixture of hexane and ethyl acetate (1:4 V/V) to give (2S,4R)-1-benzyloxycarbonyl-2-(4-hydroxy-2-butenyl)oxymethyl-4-methanesulfonyloxypyrrolidine (5.07 g).

IR (Nujol): 1680–1710 cm⁻¹

NMR (CDCl₃, δ): 2.23–2.41 (2H, m), 2.94 (3H, s), 3.32–4.27 (9H, m), 5.07 (2H, s), 5.11–5.27 (1H, m), 5.60–5.74 (2H, m), 7.27 (5H, s)

PREPARATION 24

(2S,4R)-1-Allyloxycarbonyl-2-(4-hydroxybutyl)oxymethyl-4-methanesulfonyloxypyrrolidine (1.27 g) was obtained from (2S,4R)-1-benzyloxycarbonyl-2-(4-hydroxy-2-butenyl)oxymethyl-4-methanesulfonyloxypyrrolidine in 72.2% yield in substantially the same manner as that of Preparation 16.

IR (Nujol): 3300–3500, 1735–1750, 1670–1710 cm⁻¹

NMR (CDCl₃, δ): 1.45–1.76 (4H, m), 2.24–2.46 (2H, m), 3.00 (3H, s), 3.28–3.83 (8H, m), 4.00–4.36 (2H, m), 4.51–4.66 (2H, m), 5.07–5.39 (3H, m), 5.77–6.12 (1H, m)

PREPARATION 25

(2S,4R)-1-Allyloxycarbonyl-2-(4-fluorobutyl)oxymethyl-4-methanesulfonyloxypyrrolidine (1.47 g) was obtained in 50.2% yield in substantially the same manner as that of Preparation 29.

IR (Nujol): 1685–1715 cm⁻¹

NMR (CDCl₃, δ): 1.52–1.97 (4H, m), 2.23–2.44 (2H, m), 2.98 (3H, s), 3.32–3.88 (6H, m), 4.04–4.27 (2H, m), 4.52–4.76 (3H, m), 5.13–5.37 (3H, m), 5.66–6.11 (1H, m)

PREPARATION 26

To a solution of (2S,4R)-1-benzyloxycarbonyl-2-carboxymethyloxymethyl-4-methanesulfonyloxypyrrolidine (79.4 g), 2,2-dimethyl-1,3-dioxane-4,6-dione (29.55 g) and 4-(dimethylamino)pyridine (25.05 g) in dichloromethane (635 ml) was added 1-ethyl-3-(3-dimethylaminopropyl)carbodiimide (39.3 g) at 5°–10° C. The solution was stirred at the same temperature for one hour and at ambient temperature for 18 hours. The mixture was washed with water (650 ml), 1N hydrochloric acid (650 ml), saturated aqueous sodium hydrogen carbonate (650 ml), and brine (650 ml) successively, dried over magnesium sulfate, and concentrated under reduced pressure to give a syrup. The syrup was subjected to a column chromatography on silica gel (800 g) and eluted with a mixture of methanol and dichloromethane (2:98 V/V) to give (2S,4R)-1-benzyloxycarbonyl-2-[2-(2,2-dimethyl-4,6-dioxo-1,3-dioxan-5-yl)-2-oxoethyl]oxymethyl-4-methanesulfonyloxypyrrolidine (80.98 g).

IR (CHCl₃): 1710–1675, 1650–1635 cm⁻¹

NMR (CDCl₃, δ): 1.60 (6H, s), 2.99 (3H, s), 7.32 (5H, s)

PREPARATION 27

To a solution of (2S,4R)-1-benzyloxycarbonyl-2-{2-(2,2-dimethyl-4,6-dioxo-1,3-dioxan-5-yl)-2-oxoethyl}-oxymethyl-4-methanesulfonyloxypyrrolidine (20 g) were added acetic acid (40 ml) and water (60 ml), and the mixture was heated under reflux for 40 hours. The reaction mixture was poured into a mixture of ethyl acetate (400 ml) and water (400 ml). The organic layer was separated washed in turn with water (400 ml), saturated sodium hydrogen carbonate (400 ml×2) and saturated sodium chloride, and dried over magnesium sulfate. Evaporation of the solvent gave a residue, which was chromatographed on silica gel (600 ml) eluting with 5% methanol in dichloromethane to give (2S,4R)-1-benzyloxycarbonyl-2-(2-oxopropyl)oxymethyl-4-methanesulfonyloxypyrrolidine (12.3 g).

IR (Nujol): 1670–1730 cm⁻¹

NMR (CDCl₃, δ): 2.00–2.10 (3H, m), 2.35–2.50 (2H, m), 3.01 (3H, s), 3.34–4.25 (7H, m), 5.14 (2H, s), 5.30–5.40 (1H, m), 7.36 (5H, s)

PREPARATION 28

To a solution of (2S,4R)-1-benzyloxycarbonyl-2-(2-oxopropyl)oxymethyl-4-methanesulfonyloxypyrrolidine (12 g) in ethanol (120 ml) was added by portions sodium borohydride (2.4 g) at 0° C. After 7 hours, to the reaction mixture was added dropwise acetone (20 ml) carefully at 0° C. and the solvent was evaporated in vacuo. To the resultant residue were added ethyl acetate (200 ml) and water (100 ml), the organic layer was separated, washed with brine (100 ml) and dried over magnesium sulfate. Evaporation of the solvent gave a residue, which was chromatographed on silica gel (500 ml) eluting with 5% methanol in dichloromethane (V/V) gave (2S,4R)-1-benzyloxycarbonyl-2-(2-hydroxypropyl)oxymethyl-4-methanesulfonyloxypyrrolidine (7.3 g).

IR (Nujol): 3400, 1710–1670 cm⁻¹

NMR (CDCl₃, δ): 1.09 (3H, d, J=7 250 Hz), 2.16–2.42 (2H, m), 2.97 (3H, s), 3.22–4.30 (8H, m), 5.10 (2H, s), 5.12–5.37 (1H, m), 7.27 (5H, s)

PREPARATION 29

To a solution of (2S,4R)-1-benzyloxycarbonyl-2-(2-hydroxypropyl)oxymethyl-4-methanesulfonyloxypyrrolidine (1.172 g) in dichloromethane (20 ml) was added dropwise a solution of hexafluoropropene-diethylamine complex (682 μl) in dichloromethane (5 ml) at −30° C. for 1 hour. The reaction mixture was stirred at ambient temperature for 8 hours and poured into a mixture of ice water (10 ml) and dichloromethane (10 ml). To the mixture was added 4N sodium hydroxide to adjust the pH to 6.0. The organic layer was separated, to which was added 28% solution of sodium methoxide in methanol (120 μl) and the mixture was stirred for 30 minutes. The resulting mixture was poured into a mixture of saturated sodium chloride (1.7 ml) and acetic acid (350 μl). After stirring for 10 minutes, to the resulting mixture was added 4N sodium hydroxide to adjust the pH to 6.0. The organic layer was separated, washed with brine (20 ml) and dried over magnesium sulfate. Evaporation of the solvent gave a residue, which was chromatographed on silica gel (200 ml) eluting with a mixture of hexane and ethyl acetate (2:1 V/V) to give (2S,4R)-1-benzyloxycarbonyl-2-(2-fluoropropyl)oxymethyl4-methanesulfonyloxypyrrolidine (967 mg)

IR (Nujol): 1710–1690 cm⁻¹

NMR (CDCl₃, δ): 1.67 (3H, dd, J=6.4, 23.5 Hz), 2.37 (2H,m), 3.00 (3H, s), 3.46–3.80 (6H, m), 4.10–4.26 (1H, m), 4.60–4.85 (1H, m), 5.14 (2H, s), 5.20–5.40 (1H, m), 7.36 (5H, s)

PREPARATION 30

A solution of (2S,4R)-1-benzyloxycarbonyl-2-(2-fluoropropyl)oxymethyl-4-methanesulfonyloxypyrrolidine (950 mg) in a mixture of methanol (20 ml) and concentrated hydrochloric acid (one drop) was hydrogenated under atmospheric pressure of hydrogen in the presence of 30% palladium on carbon as a catalyst at ambient temperature for 2 hours. The catalyst was filtered off and the filtrate was concentrated in vacuo to give a residue, which was dissolved in a mixture of ethyl acetate (100 ml) and water (40 ml). The aqueous layer was separated and tetrahydrofuran (40 ml) was added thereto To the solution was added dropwise allyl chloroformate (320 μl) while keeping the pH between 8-9 with 4N sodium hydroxide at 0° C. and the mixture was stirred at the same condition for one hour after addition of allyl chloroformate (320 μl). The mixture was extracted with ethyl acetate (100 ml), washed with brine (50 ml) and dried over magnesium sulfate. Evaporation of the solvent gave a residue, which was chromatographed on silica gel (100 ml) eluting with a mixture of hexane and ethyl acetate (2:1 V/V) to give (2S,4R)-1-allyloxycarbonyl-2-(2-fluoropropyl)oxymethyl-4-methanesulfonyloxypyrrolidine (360 mg).

IR (Nujol): 1710–1685 cm$^{-1}$

NMR (CDCl$_3$, δ): 1.30 (3H, dd, J=6.4, 23.5 Hz), 2.37 (2H, m), 3.00 (3H, s), 3.44–3.92 (6H, m), 4.09–4.28 (1H, m), 4.54–4.98 (3H, m), 5.18–5.40 (3H, m), 5.80–6.04 (1H, m)

PREPARATION 31

To a solution of (3S,4R)-3-[(1R)-1-(t-butyldimethylsilyloxy)ethyl]-4-{(1R)-1-methyl-2-oxo-2-(2-thioxothiazolidin-3-yl)ethyl]-2-azetidinone (3.17 g) in tetrahydrofuran (30 ml) were added 1-allyloxycarbonyl-2-(2-fluoroethyloxymethyl)-4-mercaptopyrrolidine (2.21 g) and triethylamine (1.46 ml) at 5° C., and the mixture was stirred at room temperature for 8.5 hours. Acetic acid (0.63 ml) was added to the mixture and the mixture was evaporated. The residue was dissolved in water and ethyl acetate. The organic layer was separated, washed with water, dried and evaporated. The residue was purified by chromatography on silica gel eluting with a mixture of dichloromethane and ethyl acetate (2:1 V/V) to give (3S,4S)-4-[(1R)-2-{(2S,4S)-1-allyloxycarbonyl-2-(2-fluoroethyloxymethyl)pyrrolidin-4-yl-thio}-1-methyl-2-oxoethyl]-3-{(1R)-1-(t-butyldimethylsilyloxy)ethyl}-2-azetidinone (1.82 g).

IR (Neat): 1750, 1690 cm$^{-1}$

NMR (CDCl$_3$, δ): 0.07 (6H, s), 0.87 (9H, s), 1.13 (3H, d, J=7 Hz), 1.24 (3H, d, J=7 Hz), 1.70–2.15 (1H, m), 1.30–3.28 (3H, m), 3.40–4.30 (10H, m), 4.46–4.80 (2H, m), 5.04–5.38 (2H, m), 5.65–6.10 (2H, m)

PREPARATION 32

Allyl chlorooxalate (171 mg) was dropwise added to a solution of (3S,4S)-4-[(1R)-2-{(2S,4S)-1-allyloxycarbonyl-2-(2-fluoroethyloxymethyl)pyrrolidin-4-ylthio}-1-methyl-2-oxoethyl-3-{(1R)-1-(t-butyldimethylsilyloxy)ethyl}-2-azetidinone (560 mg) in a mixture of pyridine (0.12 ml) and dichloromethane (5.6 ml) at −25° C. and the mixture was stirred for 30 minutes at the same temperature. The mixture was poured into ice-water (10 ml) and extracted with ethyl acetate. The organic layer was washed in turn with 5% aqueous sodium bicarbonate and water, dried and evaporated The resulting residue was purified by column chromatography on silica gel eluting with a mixture of n-hexane and ethyl acetate (1:1 V/V) to give (3S,4S)-1-allyloxyoxalyl-4-[(1R)-2-{(2S,4S)-1-allyloxycarbonyl-2-(2-fluoroethyloxymethyl)-pyrrolidin-4-ylthio)-1-methyl-2-oxoethyl]-3-{(1R)-1-(t-butyldimethylsilyloxy)ethyl}-2-azetidinone (665 mg).

IR (Neat): 1810, 1755, 1700 cm$^{-1}$

NMR (CDCl$_3$, δ): 0.01 (6H, s), 0.83 (9H, s), 1.18 (3H, d, J=7 Hz), 1.24 (3H, d, J=7 Hz), 1.92–2.04 (1H, m), 2.48 (1H, m), 3.17 (1H, m), 3.51–4.14 (9H, m), 4.38–4.43 (3H, m), 4.57–4.80 (5H, m), 5.19–5.44 (4H, m), 5.90 (2H, m)

PREPARATION 33

To a solution of allyl (4R)-2-diazo-4-[(2R,3S)-3-{(1R)-1-hydroxyethyl}-4-oxoazetidin-2-yl]-3-oxopentanoate (14.6 g) in dichloromethane (100 ml) was added pyridine (6.05 ml) and allyl chloroformate (10.7 ml) at −78° C. The mixture was allowed to warm to ambient temperature and stirred for one day at the same temperature. The reaction mixture was poured into ethyl acetate (100 ml) and water (50 ml), washed in turn with water (50 ml) and brine (50 ml×2), and dried over magnesium sulfate. Evaporation of the solvent gave a residue, which was chromatographed on silica gel (500 ml) eluting with a mixture of hexane and ethyl acetate (1:1 V/V) to give allyl (4R)-4-[(2R,3S)-3-{(1R)-1-allyloxycarbonyloxyethyl}-4-oxoazetidin-2-yl]-2-diazo-3-oxopentanoate (10 g).

IR (Nujol): 1740–1760, 1710 cm$^{-1}$

NMR (CDCl$_3$, δ): 1.17 (3H, d, J=6.6 Hz), 1.42 (3H, d, J=6.4 Hz), 3.17 (1H, dd, J=2, 4 Hz), 3.80–4.00 (2H, m), 4.60–4.75 (4H, m), 5.05–5.19 (1H, m), 5.24–5.45 (4H, m), 5.85–6.05 (3H, m)

PREPARATION 34

A solution of (2S,4R)-1-benzyloxycarbonyl-2-(2-hydroxyethyloxymethyl)-4-methanesulfonyloxypyrrolidine (53.0 g) in methanol (530 ml) was hydrogenated under atmospheric pressure of hydrogen at ambient temperature for 4 hours in the presence of 10% palladium on carbon (5.3 g, 50% wet). The catalyst was filtered off and the filtrate was concentrated under reduced pressure to give a syrup. The syrup was subjected to a column chromatography on silica gel (200 g) and eluted with a mixture of methanol and dichloromethane (5:95 V/V) to give (2S,4R)-2-(2-hydroxyethyloxymethyl)-4-methanesulfonyloxypyrrolidine (30.55 g).

IR (Neat): 3600–3000 cm$^{-1}$

PREPARATION 35

To a solution of (2S,4R)-2-(2-hydroxyethyloxymethyl)-4-methanesulfonyloxypyrrolidine (30.5 g) in a mixture of tetrahydrofuran (120 ml) and water (120 ml) was dropwise added a solution of allyl chloroformate (14.5 ml) in tetrahydrofuran (14.5 ml) under ice-cooling with stirring, keeping the pH between 9-10 with 4N aqueous sodium hydroxide. The mixture was stirred at the same condition for one hour and extracted with ethyl acetate (200 ml). The organic layer was dried over magnesium sulfate and evaporated under reduced pressure to give a syrup. The syrup was subjected to a column chromatography on silica gel (400 g) and eluted with a mixture of methanol and dichloromethane (2:98 V/V) to give (2S,4R)-1-allyloxycarbonyl-2-(2-hydroxyethyloxymethyl)-4-methanesulfonyloxypyrrolidine (28.03 g).

IR (Neat): 3600–3250, 1710–1670 cm$^{-1}$

NMR (CDCl$_3$, δ): 3.05 (3H, s)

PREPARATION 36-1

(2S,4S)-4-Acetylthio-1-allyloxycarbonyl-2-(2-fluoroethyloxymethyl)pyrrolidine was obtained quantitatively in substantially the same manner as that of Preparation (12-1).

IR (Neat): 1705–1690 cm$^{-1}$

NMR (CDCl$_3$, δ): 1.8–2.7 (2H, m), 2.30 (3H, s), 3.0–4.8 (12H, m), 5.1–5.5 (2H, m), 5.7–6.2 (1H, m)

PREPARATION 36-2

To a solution of (2S,4R)-1-allyloxycarbonyl-2-(2-fluoroethyloxymethyl)-4-methanesulfonyloxypyrrolidine (17.30 g) and thioacetic S-acid (5.88 ml) in 4-methyl-2-pentanone (121 ml) was added calcium hydroxide (3.05 g) below 45° C. Solvent (40 ml) was removed under reduced pressure (50–60 mmHg), at 40°–45° C. The suspension was heated at 80°–85° C. for 5 hours. After cooling, water (30 ml) was added to the suspension. The insoluble material was filtered off and washed with ethyl acetate (50 ml). The filtrate and washing were collected. The organic layer was dried over magnesium sulfate and concentrated under reduced pressure to give a syrup. The syrup was subjected to a column chromatography on silica gel (170 g) and eluted with a mixture of hexane and ethyl acetate (1:9–2:8) to give (2S,4S)-4-acetylthio-1-allyloxycarbonyl-2-(2-fluoroethyloxymethyl)pyrrolidine (13.80 g).

IR (Neat): 1705–1690 cm$^{-1}$

PREPARATION 36-3

(2S,4S)-4-Acetylthio-1-allyloxycarbonyl-2-(4-fluorobutyl)oxymethylpyrrolidine was obtained in 78.8% yield in substantially the same manner as that of Preparation 36-4.

IR (Nujol): 1705 cm$^{-1}$

NMR (CDCl$_3$, δ): 1.45–2.15 (4H, m), 2.30 (3H, s), 2.40–2.75 (1H, m), 3.02–3.25 (1H, m), 3.37–4.27 (8H, m), 4.51–4.74 (3H, m), 5.05–5.40 (3H, m), 5.64–6.10 (1H, m)

PREPARATION 36-4

To a suspension of sodium hydride (200 mg, 62.8% oil suspension) in dimethylformamide (20 ml) was added dropwise thioacetic S-acid (390 μl) at −10° C. After stirring for 30 minutes, to the reaction mixture was added dropwise a solution of (2S,4R)-1-allyloxycarbonyl-2-(2-fluoropropyl)oxymethyl-4-methanesulfonyloxypyrrolidine (1.46 g) in dimethylformamide (5 ml) and allowed to warm to 90° C. After 3 hours, the reaction mixture was poured into a mixture of ethyl acetate (60 ml), water (20 ml) and brine. The organic layer was separated, washed with brine (30 ml) and dried over magnesium sulfate. Evaporation of the solvent gave a residue, which was chromatographed on silica gel (100 ml) eluting with a mixture of hexane and ethyl acetate (2:1 V/V) to give (2S,4S)-4-acetylthio-1-allyloxycarbonyl-2-fluoropropyl)oxymethylpyrrolidine (798 mg).

IR (Nujol): 1750 cm$^{-1}$ NMR (CDCl$_3$, δ): 1.28 (3H, dd, J=6.4, 23.5 Hz), 1.83–2.60 (2H, m), 2.30 (3H, s) 3.03–4.60 (10H, m), 4.80–5.38 (3H, m) 5.64–6.10 (1H, m)

PREPARATION 36-5

To a solution of (2S,4R)-1-allyloxycarbonyl-2-(2-hydroxyethyloxymethyl)-4-methanesulfonyloxypyrrolidine (28.0 g) and thioacetic S-acid (12.47 ml) in 4-methyl-2-pentanone (168 ml) was added calcium hydroxide (6.41 g) below 45° C. Under reduced pressure (50–60 mmHg), the solvent (60 ml) was removed at 40°–50° C. The resulting suspension was heated at 80°–85° C. for 15 hours. After cooling, insoluble material was filtered off and washed with ethyl acetate (50 ml). The filtrate and washing were combined, dried over magnesium sulfate, and concentrated under reduced pressure to give a syrup. The syrup was subjected to a column chromatography on silica gel (280 g) and eluted with a mixture of methanol and dichloromethane (1:99 V/V) to give (2S,4S)-4-acetylthio-1-allyloxycarbonyl-2-(2-hydroxyethyloxymethyl)pyrrolidine (10.74 g).

IR (Neat): 3550–3200, 1715–1670 cm$^{-1}$

NMR (CDCl$_3$, δ): 2.34 (3H, s)

PREPARATION 37

(2S,4S)-1-Allyloxycarbonyl-2-(2-fluoroethyloxymethyl)-4-mercaptopyrrolidine was obtained in 70.9% yield in substantially the same manner as that of Preparation (13-1).

IR (Neat): 1710–1685 cm$^{-1}$

PREPARATION 38

To a solution of allyl (4R)-2-diazo-4-[(2R,3S)-3-{(1R)-1-(t-butyldimethylsilyloxy)ethyl}-4-oxoazetidine-2-yl]-3-oxopentanoate (13.5 g) in ethyl acetate (65 ml) was added rhodium(II) octanoate (50 mg) under refluxing in a stream of nitrogen. After 20 minutes, rhodium(II) octanoate (50 mg) was added to the mixture at the same condition. The mixture was refluxed for 30 minutes and concentrated under reduced pressure to give a syrup. The syrup was dissolved in acetonitrile (65 ml) and cooled at 0°–5° C. under atmosphere of nitrogen. To the solution was added diphenyl phosphorochloride (7.52 ml) and N,N-diisopropyl-N-ethylamine (6.31 ml) successively and the mixture was stirred at the same condition for 18 hours (solution A). To a solution of (2S,4S)-4-acetylthio-1-allyloxycarbonyl-2-(2-hydroxyethyloxymethyl)pyrrolidine (10.7 g) in acetonitrile (40.5 ml) was added a 28% solution (6.92 ml) of sodium methoxide in methanol at −10°~0° C. in a stream of nitrogen and the mixture was stirred at the same condition (solution B). To the solution A was added the solution B at −10°~0° C. in a stream of nitrogen and the mixture was stirred at −10~0° C. for one hour and then at 10°–20° C. for 3 hours. Ethyl acetate (200 ml) was added to the mixture and the mixture was washed with water (200 ml×3), dried over magnesium sulfate, and concentrated under reduced pressure to give a syrup. The syrup was subjected to a column chromatography on silica gel (300 g) and eluted with ethyl acetate to give allyl (4R,5S,6S)-3-[(2S,4S)-1-allyloxycarbonyl-2-(2-hydroxyethyloxymethyl)pyrrolidin-4-yl]thio-6-[(1R)-1-(t-butyldimethylsilyloxy)ethyl]-4-methyl-7-oxo-1-azabicyclo[3.2.0]hept-2-ene-2-carboxylate (8.80 g).

IR (Neat): 3550–3350, 1790–1765, 1725–1680 cm$^{-1}$

FAB-MS: 625 (M+)

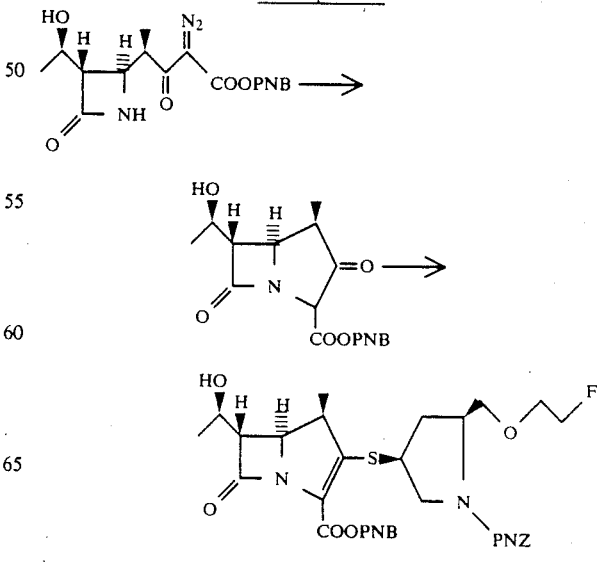

Example 1-1

-continued
Example 1-1

(PNB: 4-nitrobenzyl
PNZ: 4-nitrobenzyloxycarbonyl)

To a solution of 4-nitrobenzyl (4R)-2-diazo-4-[(2R,3S)-3-{(1R)-1-hydroxyethyl}-4-oxoazetidin-2-yl]-3-oxopentanoate (0.95 g) in dichloroethane (20 ml) was added rhodium(II) acetate (10 mg) under refluxing in a nitrogen stream. After refluxing for 1 hour, the mixture was concentrated under reduced pressure to give a residue. The residue was dissolved in anhydrous acetonitrile (20 ml). To the mixture were added diphenyl chlorophosphate (0.52 ml) and N,N-diisopropyl-N-ethylamine (0.51 ml) at −10°~−5° C. in a nitrogen stream. The mixture was stirred at the same condition for 1 hour. To the mixture were added N,N-diisopropyl-N-ethylamine (0.51 ml) and a solution of (2S,4S)-2-(2-fluoroethyloxymethyl)-4-mercapto-1-(4-nitrobenzyloxycarbonyl)pyrrolidine (0.87 g) in acetonitrile (2 ml) successively at −20° C. The mixture was stirred at the same condition for 30 minutes and then at 0°–10° C. for 3 hours. The mixture was poured into a mixture of water (50 ml) and ethyl acetate (50 ml). The organic layer was separated, washed with brine, dried over magnesium sulfate and concentrated under reduced pressure to give a syrup. The syrup was subjected to a column chromatography on silica gel (20 g) and eluted with a mixture of acetone and dichloromethane (5:95 and then, 10:90 V/V) to give 4-nitrobenzyl (4R,5S,6S)-3-[(2S,4S)-2-(2-fluoroethyloxymethyl)-1-(-4-nitrobenzyloxycarbonyl)pyrrolidin-4-yl]thio-6-[(1R)-1-hydroxyethyl]-4-methyl-7-oxo-1-azabicyclo[3.2.0]hept-2-ene-2-carboxylate (0.83 g).

IR (CHCl₃): 1765, 1705 cm⁻¹

The following compounds were obtained in substantially the same manner as that of Example (1-1).

Example 1-2

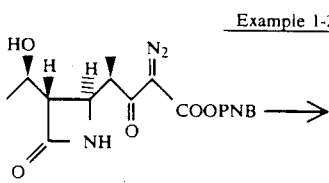
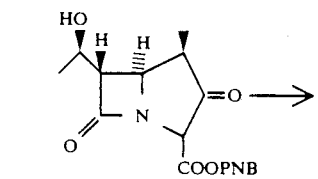
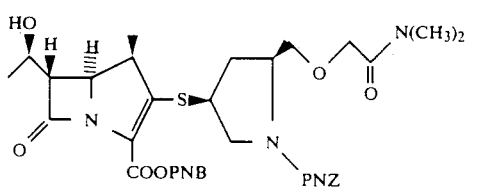

4-Nitrobenzyl (4R,5S,6S)-3-[(2S,4S)-2-(dimethylcarbamoyl)methyloxymethyl-1-(4-nitrobenzyloxycarbonyl)pyrrolidin-4-yl]thio-6-[(1R)-1-hydroxyethyl]-4-methyl-7-oxo-1-azabicyclo[3.2.0]hept-2-ene-2-carboxylate IR (CHCl₃): 3400, 1765, 1700, 1650 cm⁻¹

NMR (CDCl₃, δ): 1.30 (3H, d, J=7 Hz), 1.34 (3H, d, J=7 Hz), 2.92 (6H, s), 4.10 (2H, s)

Example 1-3

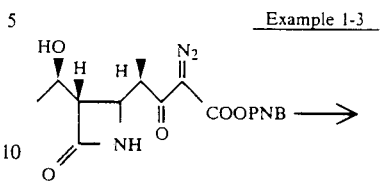
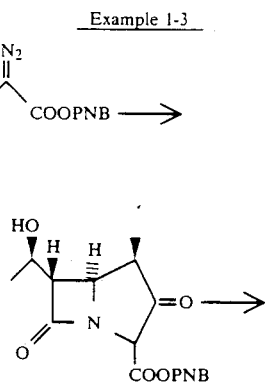
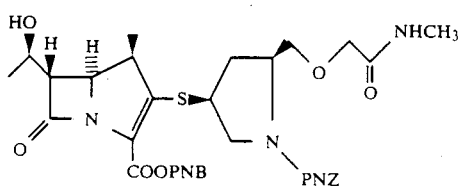

4-Nitrobenzyl (4R,5S,6S)-6-[(1R)-1-hydroxyethyl]-4-methyl-3-[(2S,4S)-2-(methylcarbamoyl)methyloxymethyl-1-(4-nitrobenzyloxycarbonyl)pyrrolidin-4-yl]thio-7-oxo-1azabicyclo[3.2.0]hept-2-ene-2-carboxylate IR (CHCl₃): 1780–1760, 1710–1665 cm⁻¹

NMR (CDCl₃, δ): 1.29 (3H, d, J=7 Hz), 1.33 (3H, d, J=7 Hz), 2.78 (3H, d, J=6 Hz), 3.92 (2H, s)

Example 1-4

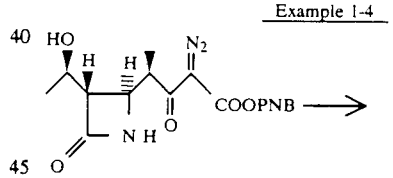
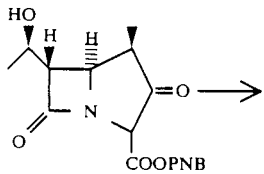
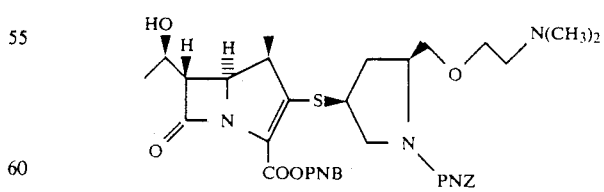

4-Nitrobenzyl (4R,5S,6S)-3-[(2S,4S)-2-{2-(dimethylamino)ethyloxmethyl}-1-(4-nitrobenzyloxycarbonyl)pyrrolidin-4-yl]thio-6-[(1R)-1-hydroxyethyl]-4-methyl-7-oxo- 1-azabicyclo[3.2.0]hept-2-ene-2-carboxylate IR (Neat): 1760–1640, 1705–1685 cm⁻¹

Example 1-5

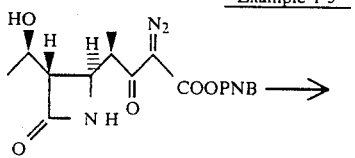
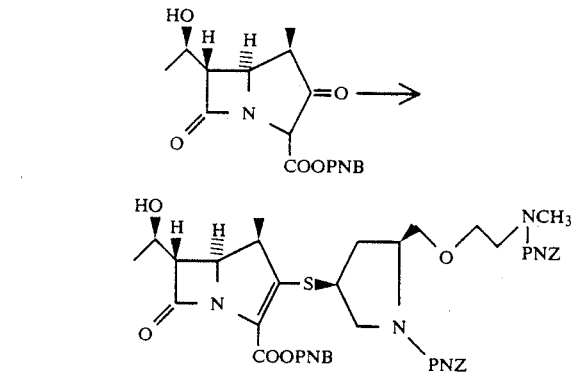

4-Nitrobenzyl (4R,5S,6S)-6-[(1R)-1-hydroxyethyl]-4-methyl-3-[(2S,4S)-2-[2-{N-methyl-N-(4-nitrobenzyloxycarbonyl)amino}ethyloxymethyl]-1-(4-nitrobenzyloxycarbonyl)pyrrolidin-4-yl]thio-7-oxo-1-azabicyclo[3.2.0]hept-2-ene-2-carboxylate IR (CHCl₃): 1770, 1710–1690 cm⁻¹

NMR (CDCl₃, δ): 1.28 (3H, d, J=7 Hz), 1.22 (3H, d, J=7 Hz), 2.97 (3H, s)

Example 1-6

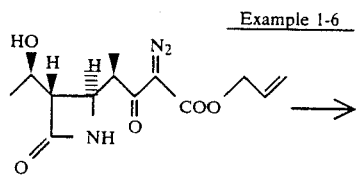
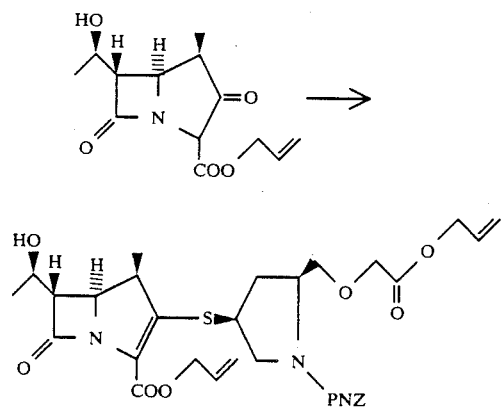

To a solution of 4-allyl (4R)-2-diazo-4-[(2R,3S)-3-{(1R)-1-hydroxyethyl}-4-oxoazetidin-2-yl]-3-oxopentanoate (1.60 g) in dichloromethane (32 ml) was added rhodium(II) octanoate (30 mg) under refluxing in a nitrogen stream. After refluxing for 1 hour, the mixture was concentrated under reduced pressure to give a residue. The residue was dissolved in anhydrous acetonitrile (32 ml). To the mixture were added diphenyl chlorophosphate (1.25 ml) and N,N-diisopropyl-N-ethylamine (1.13 ml) at −10°–5° C. in a nitrogen stream. The mixture was stirred at the same condition for 1 hour. To the mixture were added N,N-diisopropyl-N-ethylamine (1.13 ml) and a solution of (2S,4S)-2-allyloxycarbonylmethyloxymethyl-4-mercapto-1-(4-nitrobenzyloxycarbonyl)pyrrolidine (2.20 g) in acetonitrile (4 ml) successively at 0°–10° C. The mixture was stirred at the same temperature for 1 hour and at ambient temperature for 2 hours. The mixture was poured into a mixture of water (100 ml) and ethyl acetate (100 ml). The organic layer was separated, washed with brine, dried over magnesium sulfate and concentrated under reduced pressure to give a syrup. The syrup was subjected to a column chromatography on silica gel (30 g) and eluted with a mixture of acetone and dichloromethane (5:95 and then, 10:90 V/V) to give allyl (4R,5S,6S)-3-[(2S,4S)-2-(allyloxycarbonylmethyloxymethyl)-1-(4-nitrobenzyloxycarbonyl)pyrrolidin-4-yl]thio-6-[(1R)-1hydroxyethyl]-4-methyl-7-oxo-1-azabicyclo[3.2.0]hept-2-ene-2-carboxylate (1.36 g).

IR (CHCl₃): 1755, 1705 cm⁻¹

Example 2-1

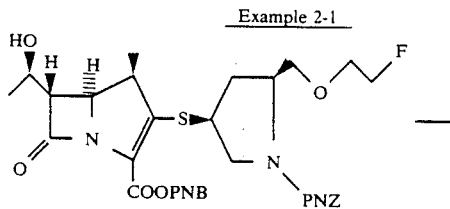
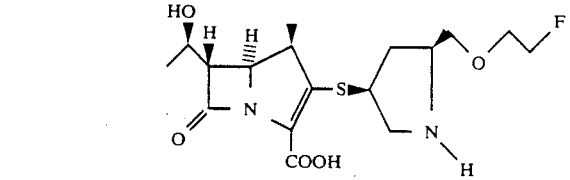

A solution of 4-nitrobenzyl (4R,5S,6S)-3-[(2S,4S)-2-(2-fluoroethyloxymethyl)-1-(4-nitrobenzyloxycarbonyl)pyrrolidin-4-yl]thio-6-[(1R)-1-hydroxyethyl]-4-methyl-7-oxo-1-azabicyclo[3.2.0]hept-2-ene-2-carboxylate (0.80 g) in a mixture of tetrahydrofuran (50 ml) and 0.1M phosphate buffer (pH 5.8) (50 ml) was stirred at ambient temperature for 5 hours in the presence of 20% palladium hydroxide on carbon (0.3 g) under atmospheric pressure of hydrogen. The catalyst was filtered off and the filtrate was concentrated under reduced pressure to remove tetrahydrofuran. The resulting aqueous solution was washed with ethyl acetate (50 ml×2) and evaporated to remove the organic solvent. The residual solution was subjected to a column chromatography on nonionic adsorption resin, "Diaion HP-20" (trademark, made by Mitsubishi Chemical Industries) (50 ml) and eluted with a mixture of acetone and water (5:95 V/V). The fractions containing the desired compound were combined and lyophilized to give (4R,5S,6S)-3-[(2S,4S)-2-(2-fluoroethyloxymethyl)pyrrolidin-4-yl]thio-6-[(1R)-1-hydroxyethyl]-4-methyl-7-oxo-1-azabicyclo[3.2.0]hept-2-ene-2-carboxylic acid (0.20 g).

mp: 155° C. (dec.)

IR (KBr): 1760–1730 cm⁻¹

NMR (D₂O, δ): 1.21 (3H, d, J=7 Hz), 1.28 (3H, d, J=7 Hz)

FD-MS: 389 (M⁺+1)

The following compounds were obtained in substantially the same manner as that of Example (2-1).

Example (2-2)

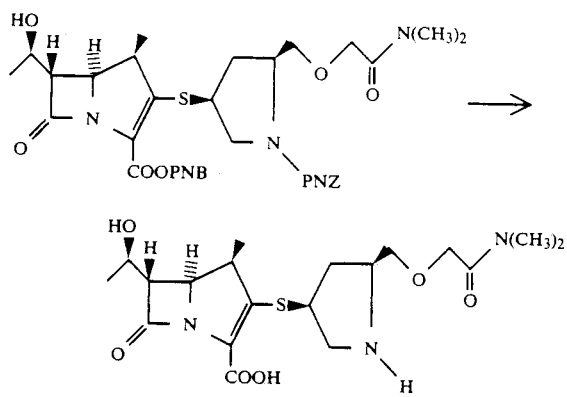

(4R,5S,6S)-3-[(2S,4S)-2-{(Dimethylcarbamoyl)methyloxymethyl}pyrrolidin-4-yl]thio-6-[(1R)-1-hydroxyethyl]-4-methyl-7-oxo-1-azabicyclo[3.2.0]hept-2-ene-2-carboxylic acid mp: 150° C. (dec.)

IR (KBr): 1750–1730 cm$^{-1}$

NMR (D$_2$O, δ): 1.20 (3H, d, J=7 Hz), 1.27 (3H, d, J=7 Hz), 2.88 (6H, s)

FD-MS: 428 (M+)

Example (2-3)

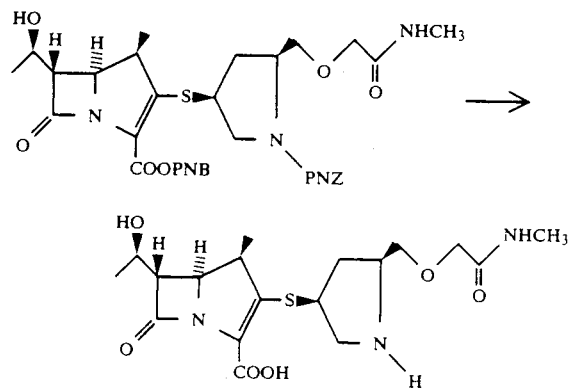

(4R,5S,6S)-6-[(1R)-1-Hydroxyethyl]-4-methyl-3-(2S,4S)-2-{(methylcarbamoyl)methyloxymethyl}pyrrolidin4-yl]thio-7-oxo-1-azabicyclo[3.2.0]hept-2-ene-2-carboxylic acid IR (KBr): 1760–1720 cm$^{-1}$ NMR (D$_2$O, δ): 1.21 (3H, d, J=7 Hz), 1.28 (3H, d, J=7 Hz), 2.80 (2H, s)

FD-MS: 414 (M+ +1)

Example (2-4)

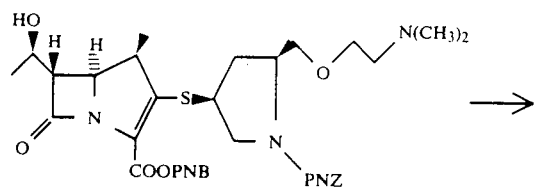

-continued
Example (2-4)

A solution of 4-nitrobenzyl (4R,5S,6S)-3-[(2S,4S)-2-{2-(dimethylamino)ethyloxymethyl}-1-(4-nitrobenzyloxycarbonyl)pyrrolidin-4-yl]thio-6-[(1R)-1-hydroxyethyl]-4-methyl-7-oxo-1-azabicyclo[3.2.0]hept-2-ene-2-carboxylate (1.48 g) in a mixture of tetrahydrofuran (60 ml) and 0.3 M acetate buffer (pH 5.8) (60 ml) was stirred at ambient temperature for 6 hours in the presence of 20% palladium hydroxide on carbon (0.5 g) under atmospheric pressure of hydrogen. The catalyst was filtered off and the filtrate was concentrated under reduced pressure to remove the tetrahydrofuran The resulting aqueous solution was washed with ethyl acetate (50 ml×3) and evaporated to remove the organic solvent The residual solution was subjected to a column chromatography on nonionic adsorption resin, "Diaion HP-20" (60 ml) and eluted with a mixture of acetone and water (2:98 V/V). The fractions containing the desired compound were collected and 0.5M aqueous acetic acid (1.5 ml) was added to the solution The solution was lyophilized to give (4R,5S,6S)-3-[(2S,4S)-2-{2--(dimethylamino)ethyloxymethyl}pyrrolidin-4-yl]thio-6-[(1R)-1-hydroxyethyl]-4-methyl-7-oxo-1-azabicyclo[3.2.0]hept-2-ene-2-carboxylic acid monoacetate (0.14 g).

mp: 90° C. (dec.)

NMR (D$_2$O, δ): 1.97 (3H, s), 2.94 (6H, s)

FD-MS: 414 (M+-CH$_3$CO$_2$H)

The following compound was obtained in substantially the same manner as that of Example (2-4).

Example (2-5)

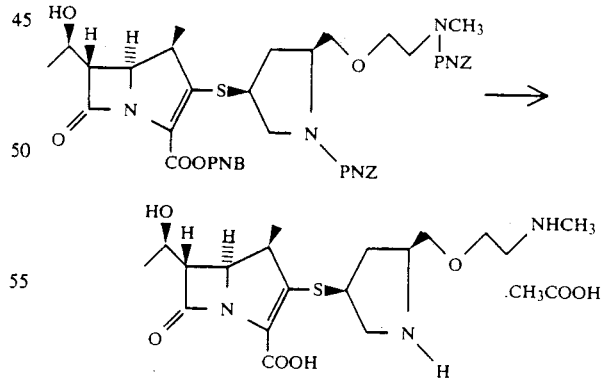

(4R,5S.6S)-6-[(1R)-1-Hydroxyethyl]-4-methyl-3-[(2S,4S)-2-{2-(methylamino)ethyloxymethyl}pyrrolidin-4-yl]thio-7-oxo-1-azabicyclo[3,2,0]hept-2-ene-2-carboxylic acid monoacetate mp: 80° C. (dec.)

IR (KBr): 1755–1735 cm$^{-1}$

NMR (D$_2$O, δ): 1.21 (3H, d, J=7 Hz), 1.28 (3H, d, J=7 Hz), 1.92 (3H, s), 1.75 (3H, s)

FD-MS: 400 (M+-CH$_3$CO$_2$H)

Example (2-6)

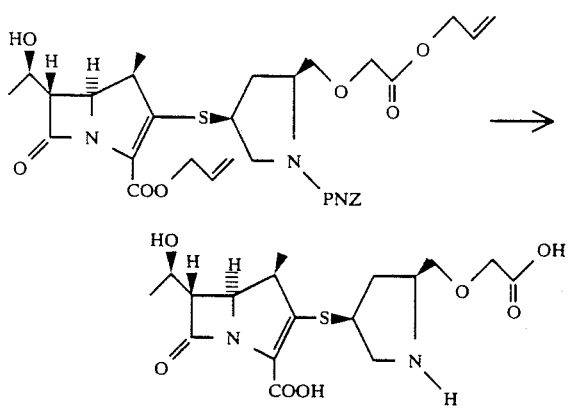

To a solution of allyl (4R,5S,6S)-3-[(2S,4S)-2-(allyloxycarbonylmethyloxymethyl)-1-(4-nitrobenzyloxycarbonyl)pyrrolidin-4-yl]thio-6-[(1R)-1-hydroxyethyl]-4-methyl-7-oxo-1azabicyclo[3.2.0]hept-2-ene-2-carboxylate (1.33 g), sodium 2-ethylhexanoate (0.75 g) and triphenylphosphine (0.21 g) in tetrahydrofuran (60 ml) was added tetrakis(triphenylphosphine)palladium(O) (0.25 g), at ambient temperature. The mixture was stirred at the same temperature for 1 hour. To the mixture was added 0.3M acetate buffer (pH 5.8) (60 ml). The mixture was stirred at ambient temperature for 6 hours in the presence of 20% palladium hydroxide on carbon (0.5 g) under atmospheric pressure of hydrogen. The catalyst was filtered off and the filtrate was concentrated under reduced pressure to remove the tetrahydrofuran. The resulting aqueous solution was washed with ethyl acetate (60 ml x 3)and evaporated to remove the organic solvent. The residual solution was subjected to a column chromatography on nonionic adsorption resin, "Diaion HP-20" [60 ml]and eluted with a mixture of acetone and water (2:98 V/V). The fractions containing the desired compound were collected and lyophilized to give (4R,5S,6S)-3-[(2S,4S)-2-(carboxymethyloxymethyl)pyrrolidin-4-yl]thio-6-[(1R)-1-hydroxyethyl]-4-methyl-7-oxo-1-azabicyclo[3.2.0]hept-2-ene-2-carboxylic acid (0.37 g).

mp: 175° C. (dec.)

IR (KBr): 1750–1730 cm$^{-1}$

NMR (D$_2$O, δ): 1.18 (3H, d, J=7 Hz), 1.27 (3H, d, J=7 Hz)

FD-MS: 401 (M$^+$+1

Example (3-1)

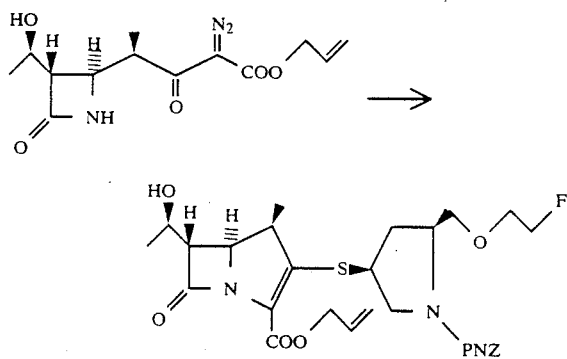

To a solution of allyl (4R)-2-diazo-4-[(2R,3S)-3-{(1R)-1-hydroxyethyl}-4-oxoazetidin-2-yl]-3-oxopentanoate (1.75 g) in ethyl acetate (17 ml) was added rhodium(II) octanoate (50 mg) under refluxing in a stream of nitrogen. The mixture was refluxed for one hour and concentrated under reduced pressure to give a syrup. The syrup was dissolved in acetonitrile (17 ml) and cooled to 0°~5° C. under atmosphere of nitrogen. To the solution was added diphenyl chlorophosphate (1.35 ml) and N,N-diisopropyl-N-ethylamine (1.25 ml) successively and the mixture was stirred at the same condition for 18 hours. To this mixture were added a solution of (2S,4S)-2-(2-fluoroethyl)-oxymethyl-4-mercapto-1-(4-nitrobenzyloxycarbonyl)-pyrrolidine (2.10 g) in acetonitrile (2 ml) and N,N-diisopropyl-N-ethylamine (1.25 ml) successively at 0°-5° C. The mixture was stirred at 0°-5° C. for one hour and at ambient temperature for 3 hours and poured into a mixture of ethyl acetate (80 ml) and water (80 ml). The organic layer was washed in turn with water (80 ml) and brine (80 ml), dried over magnesium sulfate, and concentrated under reduced pressure to give a syrup. The syrup was subjected to a column chromatography on silica gel (40 g) and eluted with a mixture of acetone and dichloromethane (1:9 V/V) to give allyl (4R,5S,6S)-3-[(2S,4S)-2-(2-fluoroethyloxy-methyl)-1-(4-nitrobenzyloxycarbonyl)pyrrolidin-4-yl]thio-6-[(1R)-1-hydroxyethyl]-4-methyl-7-oxo-1-azabicyclo-[3.2.0]hept-2-ene-2-carboxylate (2.10 g).

IR (CH$_2$Cl$_2$): 3450–3300, 1775–1600, 1710–1685 cm$^{-1}$

NMR (CDCl$_3$, δ): 1.25 (3H, d, J=7 Hz), 1.35 (3H, d, J=7 Hz), 5.22 (2H, s), 5.7–6.2 (1H, m), 7.48 (2H, d, J=8 Hz), 8.22 (2H, d, J=8 Hz)

Example (3-2)

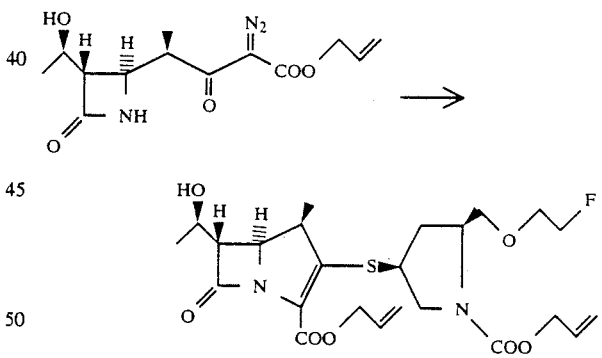

To a solution of allyl (4R)-2-diazo-4-[(2R,3S)-3-{(1R)-1-hydroxyethyl}-4-oxoazetidin-2-yl]-3-oxopentanoate (3.80 g) in ethyl acetate (20 ml) was added rhodium(II) octanoate (20 mg) under reflux in a stream of nitrogen. After 20 minutes, rhodium(II) octanoate (20 mg) was added to the mixture at the same condition. The mixture was refluxed for 40 minutes and concentrated under reduced pressure to give a syrup. The syrup was dissolved in acetonitrile (20 ml) and cooled at 0°-5° C. under atmosphere of nitrogen. To the solution was added diphenyl chlorophosphate (2.94 ml) and N,N-diisopropyl-N-ethylamine (2.69 ml) successively and the mixture was stirred at the same condition for 18 hours. To this mixture were added a solution of (2S,4S)-1-allyloxycarbonyl-2-(2-fluoroethyloxymethyl)-4-mercaptopyrrolidine (3.65 g) in acetonitrile (4 ml) and N,N- diisopropyl-N-ethylamine (2.69 ml) successively at 0°~5° C. The mixture was stirred at 0°-5° C. for one hour and at ambient temperature for 3 hours, and then poured into a mixture of ethyl acetate (100 ml) and water (60 ml). The organic layer was washed with water (60 ml) and brine (60 ml) in turn, dried over magnesium sulfate and concentrated under reduced pressure to give a syrup. The syrup was subjected to a column chromatography on silica gel (60 g) and eluted with a mixture of hexane and ethyl acetate (4:1 V/V) to give allyl (4R,5S,6S)-3-[(2S,4S)-1-allyloxycarbonyl-2-(2-fluoroethyloxymethyl)pyrrolidin-4-yl]thio-6-[(1R)-1-hydroxyethyl]-4-methyl-7-oxo-1-azabicyclo[3.2.0]hept-2-ene-2-carboxylate (2.58 g).

IR (Neat): 1785–1745, 1710–1670 cm⁻¹

Example (3-3)

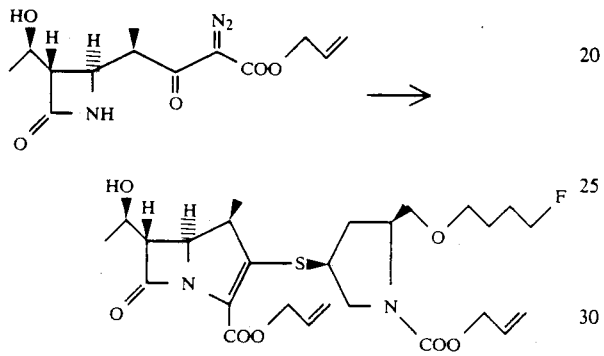

Allyl (4R,5S,6S)-3-[(2S,4S)-1-allyloxycarbonyl-2-(4-fluorobutyl)oxymethylpyrrolidin-4-yl]thio-6-[(1R)-1-hydroxyethyl]-4-methyl-7-oxo-1-azabicyclo[3.2.0]hept-2-ene-2-carboxylate was obtained in 32.8% yield in substantially the same manner as that of Preparation 38.

IR (Nujol): 3350–3500, 1750, 1685–1710 cm⁻¹
NMR (CDCl₃, δ): 1.12–2.05 (10H, m), 2.24–2.71 (1H, m), 3.05–4.30 (14H, m), 4.50–4.75 (5H, m), 5.13–5.51 (4H, m), 5.65–6.12 (2H, m)

Example (3-4)

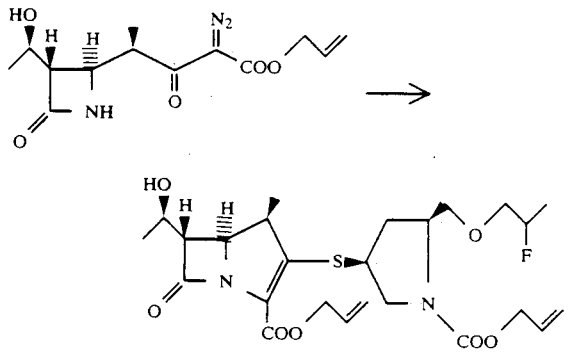

To a solution of allyl (4R)-2-diazo-4-[(2R,3S)-3-{(1R)-1-hydroxyethyl}-4-oxoazetidin-2-yl]-3-oxopentanoate (621 mg) in ethyl acetate (10 ml) was added rhodium(II) octanoate (10 mg) under nitrogen atmosphere, which was heated under reflux for 30 minutes. The solvent was evaporated and the remaining ethyl acetate was removed as the acetonitrile (10 ml) azeotrope to give a residue, which was dissolved in acetonitrile (10 ml) and cooled to 0° C. under nitrogen atmosphere. To the solution were added diphenyl chlorophosphate (480 μl), N,N-diisopropyl-N-ethylamine (421 μl) and N,N-dimethylacetamide (5 ml), and the solution was stirred for 10 hours at 0° C. To the solution was added at 0° C. a reaction mixture of (2S,4S)-4-acetylthio-1-allyloxycarbonyl-2-(2-fluoropropyl)oxymethylpyrrolidine (790 mg) and 28% sodium methoxide (485 μl) in acetonitrile (5 ml) which reaction had been carried out at −20° C. for 15 minutes. The reaction mixture was allowed to warm at ambient temperature and stirred for 5 hours, which was poured into a mixture of ethyl acetate (50 ml) and water (20 ml). The organic layer was separated, washed with brine, dried over magnesium sulfate and evaporated in vacuo to give a residue, which was chromatographed on silica gel (100 ml) eluting with a mixture of hexane and ethyl acetate (1:1–1:2 V/V) to give allyl (4R,5S,6S)-3-[(2S,4S)-1-allyloxycarbonyl-2-(2-fluoropropyl)oxymethylpyrrolidin-4-yl]thio-6-[(1R)-1-hydroxyethyl]-4-methyl-7-oxo-1-azabicyclo[3.2.0]hept-2-ene-2-carboxylate (300 mg).

IR (Nujol): 3350–3400, 1770, 1690–1710 cm⁻¹
NMR (CDCl₃, δ): 1.16–1.45 (9H, m), 1.80–2.67 (2H, m), 3.12–4.23 (13H, m), 4.45–4.78 (4H, m), 5.08–5.50 (4H, m), 5.67–6.00 (2H, m)

Example (3-5)

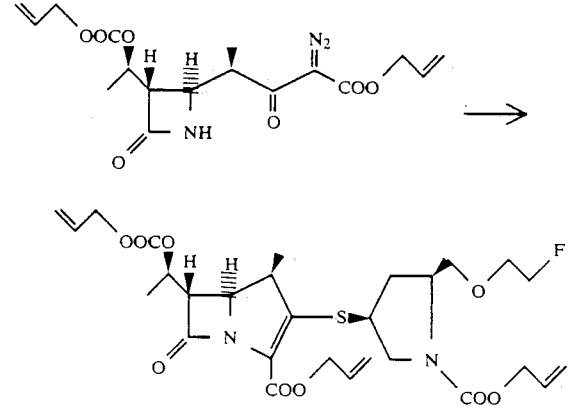

To a solution of allyl (4R)-4-[(2R,3S)-3-{(1R)-1-allyloxycarbonyloxyethyl}-4-oxoazetidin-2-yl]-2-diazo-3-oxopentanoate (1.8 g) in ethyl acetate (30 ml) was added rhodium(II) octanoate (21.9 g) under nitrogen atmosphere. The mixture was heated under reflux for 30 minutes and then cooled to −20° C. To the reaction mixture were added methanesulfonyl chloride (405 μl) followed by dropwise addition of triethylamine (793 μl), and the mixture was stirred for 1 hour. To this mixture was added at 0° C. a reaction mixture of (2S,4S)-4-acetylthio-1-allyloxycarbonyl-2-(2-fluoroethyl)oxymethylpyrrolidine (1.62 g) and a 28% solution of sodium methoxide (957 μl) in acetonitrile which reaction had been carried out at −20° C. The reaction mixture was allowed to warm to ambient temperature and stirred for 3 hours, which was poured into a mixture of ethyl acetate (100 ml) and water (50 ml). The organic layer was separated, washed with brine and dried over magnesium sulfate. Evaporation of the solvent gave a residue, which was chromatographed on silica gel (100 ml) eluting with a mixture of hexane and ethyl acetate (2:1 V/V) to give allyl (4R,5S,6S)-6-[(1R)-1-allyloxycarbonyloxyethyl]-3-[(2S,4S)-1-allyloxycarbonyl-2-2-fluoroethyl)oxymethylpyrrolidin-4-yl]thio-4- methyl-7-oxo-1-azabicyclo[3.2.0]hept-2-ene-2-carboxylate (1.72 g).

IR (Nujol): 1750–1780, 1670–1710 cm$^{-1}$

NMR (CDCl$_3$, δ): 1.25 (3H, d, J=7 Hz), 1.40 (3H, d, J=7 Hz), 2.30–2.50 (1H, m), 3.10–4.28 (15H, m), 4.45–4.82 (6H, m), 4.95–5.48 (6H, m), 5.68–6.12 (3H, m)

Example 4

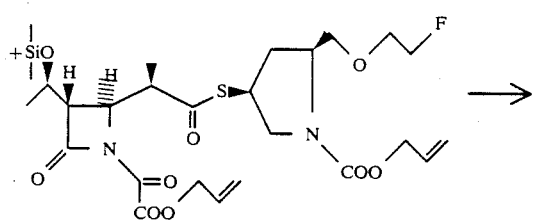

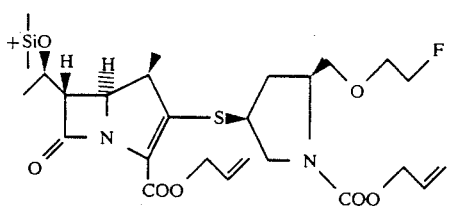

To a solution of (3S,4S)-1-allyloxyoxalyl-4-[(1R)-2--{(2S,4S)-1-allyloxycarbonyl-2-(2-fluoroethyloxymethyl)pyrrolidin-4-ylthio}-1-methyl-2-oxoethyl]-3-{(1R)-1-(t-butyldimethylsilyloxy)ethyl)}-2-azetidinone (640 mg) in toluene (2 ml) was added triethyl phosphite (0.65 ml) and the solution was stirred at 90°–95° C. for 2.5 hours and evaporated under reduced pressure. Xylene (6 ml) was added thereto and the mixture was refluxed for 8 hours. The residue was purified by column chromatography on silica gel eluting with a mixture of n-hexane and ethyl acetate (2:1 V/V) to give allyl (4R,5S,6S)-3-[(2S,4S)-1-allyloxycarbonyl-2-(2-fluoroethyloxymethyl)pyrrolidin-4yl]}thio-6-[(1R)-1-(t-butyldimethylsilyloxy)ethyl]-(4-methyl-7-oxo-1-azabicyclo[3.2.0]hept-2-ene-2-carboxylate (250 mg).

IR (Neat): 1760, 1695 cm$^{-1}$

NMR (CDCl$_3$, δ): 0.08 (6H, s), 0.87 (9H, s), 1.24 (6H, d, J=7 Hz), 1.72–2.18 (1H, m), 2.30–2.65 (1H, m), 3.10–4.34 (13H, m), 4.43–4.82 (5H, m), 5.02–5.50 (4H, m), 5.64–6.13 (2H, m)

Example 5

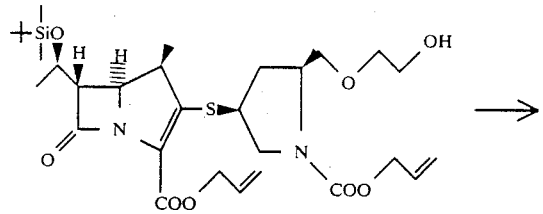

-continued
Example 5

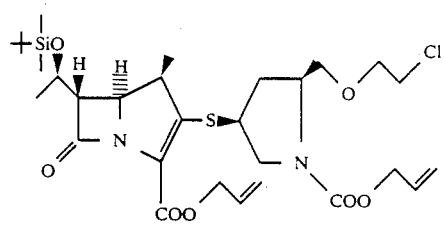

A solution of allyl (4R,5S,6S)-3-[(2S,4S)-1-allyloxycarbonyl-2-(2-hydroxyethyloxymethyl)pyrrolidin-4-yl]thio-6-[(1R)-1-(t-butyldimethylsilyloxy)ethyl]-4-methyl-7-oxo-1-azabicyclo[3.2.0]hept-2-ene-2-carboxylate (4.50 g) and triphenylphosphine (3.78 g) in carbon tetrachloride (90 ml) was heated under reflux for 14 hours. Resulting insoluble material was filtered off and the filtrate was concentrated under reduced pressure to give a syrup. The syrup was chromatographed on silica gel (90 g) and eluted with a mixture of ethyl acetate and hexane (40:60 V/V) to give allyl (4R,5S,6S)-3-[(2S,4)-1-allyloxycarbonyl-2-(2- chloroethyloxymethyl)pyrrolidin-4-yl]thio-6-[(1R)-1-(t-butyldimethylsilyloxy)ethyl]-4-methyl-7-oxo-1-azabicyclo-[3.2.0]hept-2-ene-2-carboxylate (2.42 g).

IR (Neat): 1780–1765, 1710–1690 cm$^{-1}$
NMR (CDCl$_3$, δ): 0.08 (6H, s), 0.88 (9H, s)

Example (6-1)

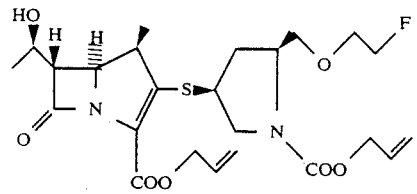

To a solution of allyl (4R,5S,6S)-3-[(2S,4S)-1-allyloxycarbonyl-2-(2-fluoroethyloxymethyl)pyrrolidin-4-yl]thio-6-[(1R)-1-(t-butyldimethylsilyloxy)ethyl]-4-methyl-7-oxo-1-azabicyclo[3.2.0]hept-2-ene-2-carboxylate (250 mg) in tetrahydrofuran (5 ml) were added 1M tetrabutylammonium fluoride in tetrahydrofuran (1.2 ml) and acetic acid (0.8 ml), and the solution was stirred at room temperature for 23 hours. Water (10 ml) and ethyl acetate (10 ml) were added and stirred for 5 minutes. The organic layer was separated washed with brine (10 ml), dried and evaporated to give an oily residue, which was chromatographed on silica gel eluting with a mixture of n-hexane and ethyl acetate (1:1 V/V) to give allyl (4R,5S,6S)-3-[(2S,4S)-1-allyloxycarbonyl-2-(2-fluoroethyloxymethyl)pyrrolidin-4-yl]thio-6-[(1R)-1-hydroxyethyl]-4-methyl-7-oxo-1-azabicyclo[3.2.0]hept-2-ene-2-carboxylate (110 mg), which was identified by comparison of the infrared spectrum with that of an authentic sample.

Example (6-2)

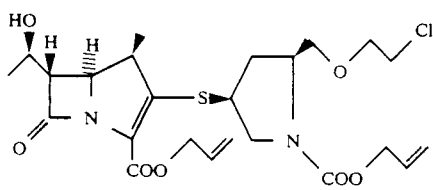

To a solution of allyl (4R,5S,6S)-3-[(2S,4S)-1-allyl oxycarbonyl-2-(2-chloroethyloxymethyl)pyrrolidin-4-yl]thio-6-[(1R)-1-(t-butyldimethylsilyloxy)ethyl]-4-methyl-7-oxo-1-azabicyclo[3.2.0]hept-2-ene-2-carboxylate (0.72 g) in tetrahydrofuran (7.2 ml) were added glacial acetic acid (0.65 ml) and a 1M solution (5.6 ml) of tetrabutylammonium fluoride in tetrahydrofuran in a stream of nitrogen, and the mixture was stirred at room temperature for 10 hours. To the mixture was added ethyl acetate (50 ml). The solution was washed with water (50 ml×3), dried over magnesium sulfate and concentrated under reduced pressure to give a syrup. The syrup was chromatographed on silica gel (10 g) and eluted with a mixture of hexane and ethyl acetate (80:20 V/V) to give allyl (4R,5S,6S)-3-[(2S,4S)-1-allyloxycarbonyl-2-(2-chloroethyloxymethyl)pyrrolidin-4-yl]thio-6-[(1R)-1-hydroxyethyl]-4-methyl-7-oxo-1-azabicyclo[3.2.0]hept-2-ene-2-carboxylate (0.30 g).

IR (Neat): 3550–3300, 1780–1760, 1710–1675 cm$^{-1}$
NMR (CDCl$_3$, δ): 1.27 (3H, d, J=7.5 Hz), 1.33 (3H, d, J=7.5 Hz)
FAB-MS: 529, 531 (M$^+$ +1)

Example (7-1)

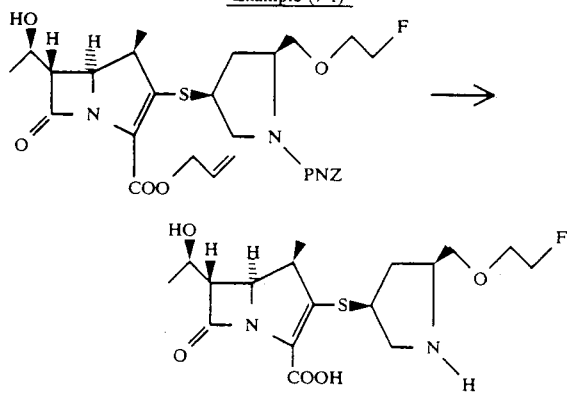

To a solution of allyl (4R,5S,6S)-3-[(2S,4S)-2-(2-fluoroethyloxymethyl)-1-(4-nitrobenzyloxycarbonyl)-pyrrolidin-4-yl]thio-6-[(1R)-1-hydroxyethyl]-4-methyl-7-oxo-1-azabicyclo[3.2.0]hept-2-ene-2-carboxylate (4.00 g), sodium 2-ethylhexanoate (1.21 g), and triphenylphosphine (0.35 g) in tetrahydrofuran (120 ml) was added tetrakis(triphenylphosphine)palladium(0) (0.77 g) at ambient temperature in a stream of nitrogen. The mixture was stirred at the same condition for one hour. To the mixture was added 0.1M phosphate buffer (pH 6.0) (120 ml). The mixture was stirred in the presence of 20% palladium hydroxide on carbon (0.8 g) under atmospheric pressure of hydrogen at ambient temperature for 4 hours. The catalyst was filtered off and the filtrate was concentrated under reduced pressure to remove the tetrahydrofuran. An aqueous solution was washed with ethyl acetate (100 ml×3) and the organic solvent was removed by evaporation. The residual solution was subjected to a column chromatography on nonionic adsorption resin, "Diaion HP-20" (100 ml) and eluted with a mixture of acetone and water (7:93 V/V). The fractions containing the desired compound were collected and lyophilized to give (4R,5S,6S)-3-[(2S,4S)-2-(2-fluoroethyloxymethyl)pyrrolidin-4-yl]thio-6-[(1R)-1-hydroxyethyl]-4-methyl-7-oxo-1-azabicyclo[3.2.0]hept-2-ene-2-carboxylic acid as a solid (1.36 g).

Example (7-2)

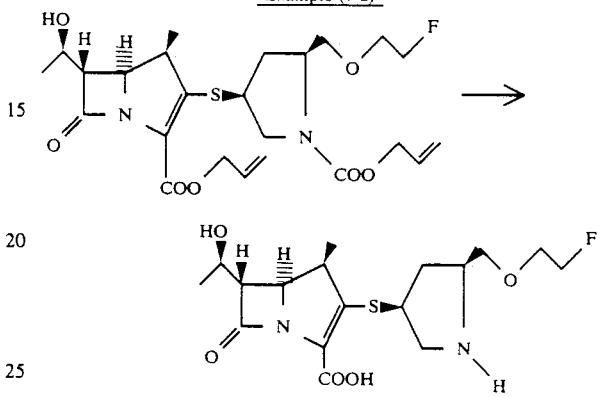

Tetrakis(triphenylphosphine)palladium(0) [0.32 g] was added to a solution of allyl (4R,5S,6S)-3-[(2S,4S)-1-allyloxycarbonyl-2-(2-fluoroethyloxymethyl)pyrrolidin-4-yl]thio-6-[(1R)-1-hydroxyethyl]-4-methyl-7-oxo-1-azabicyclo[3.2.0]hept-2-ene-2-carboxylate (2.35 g), morpholine (0.84 ml) and triphenylphosphine (0.24 g) in a mixture of water (3 ml), ethanol (12 ml) and tetrahydrofuran (35 ml) at ambient temperature in a stream of nitrogen, and the mixture was stirred at the same condition for 2 hours to give precipitates. The precipitates were collected by filtration, washed with tetrahydrofuran, and dried over phosphorus pentoxide to give (4R,5S,6S)-3-[(2S,4S)-2-(2-fluoroethyloxymethyl)pyrrolidin-4-yl]thio-6-[(1R)1-hydroxyethyl[-4-methyl-7-oxo-1-azabicyclo[3.2.0]hept-2-ene-2-carboxylic acid (0.67 g).

mp: 155° C. (dec.)
IR (Nujol): 1760–1730 cm$^{-1}$

Example (7-3)

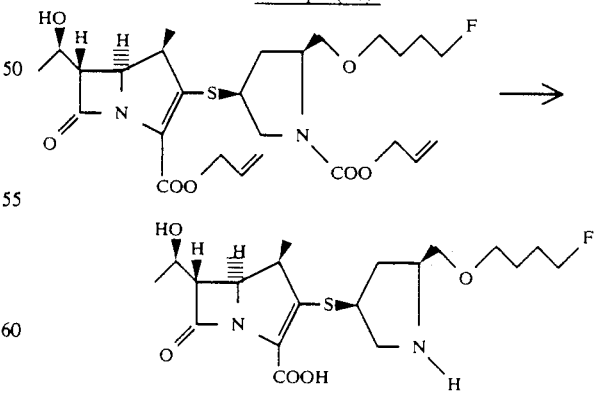

(4R,5S,6S)-3-[(2S,4S)-2-(4-Fluorobutyl)oxymethyl-pyrrolidin-4-yl]thio-6-[(1R)-1-hydroxyethyl]-4-methyl-7-oxo-1-azabicyclo[3.2.0]hept-2-ene-2-carboxylic acid was obtained in 91% yield in substantially the same manner as that of Example 7-2).

IR (Nujol): 1750 cm$^{-1}$

NMR (CDCl$_3$, δ): 1.21 (3H, d, J=7 Hz), 1.27 (3H, d, J=7 Hz), 1.53-1.92 (4H, m), 2.47-2.86 (1H, m), 3.27-5.00 (16H, m)

Example (7-4)

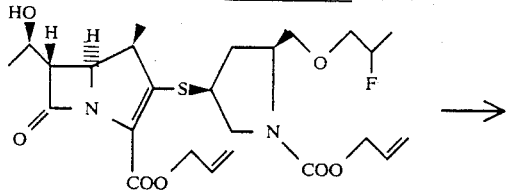

To a solution of allyl (4R,5S,6S)-3-[(2S,4S)-1-allyloxycarbonyl-2-(2-fluoropropyl)oxymethylpyrrolidin-4-yl]thio-6-[(1R)-1-hydroxyethyl]-4-methyl-7-oxo-1-azabicyclo[3.2.0]hept-2-ene-2-carboxylate (280 mg) in a mixture of tetrahydrofuran (2 ml), ethanol (1 ml) and water (200 µl) were added triphenylphosphine (14.2 mg), morpholine (125 µl) and tetrakis(triphenylphosphine)palladium(0) (12.2 mg) at room temperature for 3 hours under nitrogen atmosphere. The reaction mixture was poured into a mixture of ethyl acetate (20 ml) and water (10 ml). The aqueous layer was separated and concentrated in vacuo to give a residual solution, which was chromatographed on "Diaion HP-20" eluting in turn with water and 5% aqueous acetone. The fractions containing the desired compound were collected and lyophilized to give (4R,5S,6S)-3-[(2S,4S)-2-(2-fluoropropyl)oxymethylpyrrolidin-4-yl]thio-6-[(1R)-1-hydroxyethyl]-4-methyl-7-oxo-1-azabicyclo[3.2.0]hept-2-ene-2-carboxylic acid (216 mg).

IR (Nujol): 3200-3400, 1750-1760 cm$^{-1}$

NMR (D$_2$O, δ): 1.00-1.45 (9H, m), 3.20-4.10 (14H, m)

Example (7-5)

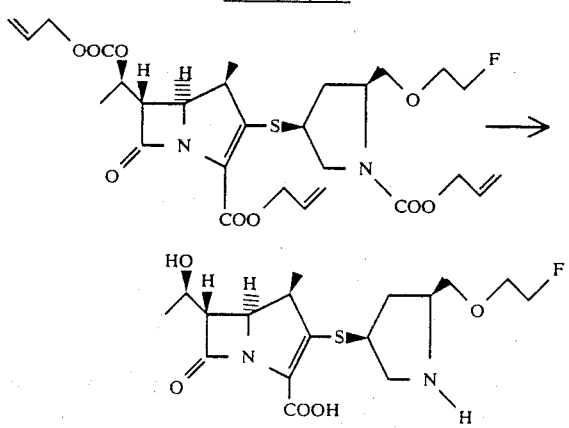

To a solution of allyl (4R,5S,6S)-6-[(1R)-1-allyloxycarbonyloxyethyl]-3-[(2S,4S)-1-allyloxycarbonyl-2-(2-fluoroethyl)oxymethylpyrrolidin-4-yl]thio-4-methyl-7-oxo-1-azabicyclo[3.2.0]hept-2-ene-2-carboxylate (372 mg) in a mixture of tetrahydrofuran (3.2 ml), ethanol (1.6 ml) and water (800 µl) were added triphenylphosphine (17 mg), morpholine (216 µl) and tetrakis(triphenylphosphine)palladium(0) (72 mg) at room temperature for 3 hours under nitrogen atmosphere. The reaction mixture was poured into a mixture of ethyl acetate (40 ml) and water (20 ml). The aqueous layer was separated and concentrated in vacuo to give a residual solution, which was chromatographed on "Diaion HP-20" eluting in turn with water and 10% aqueous acetone. The fractions containing the desired compound were collected and lyophilized to give (4R,5S,6S)-3-[(2S,4S)-2-(2-fluoroethyl)oxymethylpyrrolidin-4-yl]thio-6-[(1R)-1-hydroxyethyl]-4-methyl-7-oxo-1-azabicyclo[3.2.0]hept-2-ene-2-carboxylic acid (20 mg).

IR (Nujol): 3350-3050, 1730-1770 cm$^{-1}$

NMR (D$_2$O, δ): 1.21 (3H, d, J=7 Hz), 1.28 (3H, d, J=8 Hz), 1.5-2.0 (1H, m), 2.5-2.9 (1H, m)

Example (7-6)

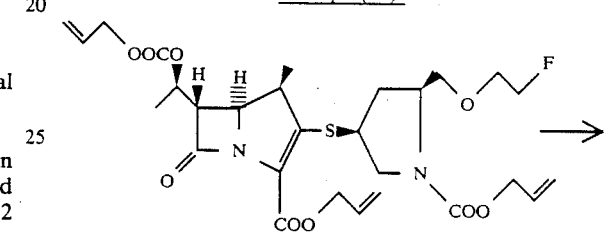

To a solution of allyl (4R,5S,6S)-6-[(1R)-1-allyloxycarbonyloxyethyl-3-[(2S,4S)-1-allyloxycarbonyl-2-(2-fluoroethyl)oxymethylpyrrolidin-4-yl]thio-4-methyl-7-oxo-1-azabicyclo[3.2.0]hept-2-ene-2-carboxylate (350 mg) in a mixture of 4-methyl-2-pentanone (4.2 ml), ethanol (2.1 ml) and water (170 µl) was added triphenylphosphine (16 mg), 5,5-dimethyl-1,3-cyclohexanedione (255 mg) and tetrakis(triphenylphosphine)palladium(0) (68 mg) at room temperature for 3 hours under nitrogen atmosphere. Evaporation of the solvent gave a residue, which was dissolved in a mixture of ethyl acetate (40 ml) and water (20 ml). The aqueous layer was separated and concentrated. The residual solution was chromatographed on "Diaion HP-20" eluting with 10% aqueous acetone. The fractions containing the desired compound were collected, and lyophilized to give (4R,5S,6S)-3-[(2S,4S)-2-(2-fluoroethyl)oxymethylpyrrolidin-4-yl]thio-6-[(1R)-1-hydroxyethyl]-4-methyl-7-oxo-1-azabicyclo[3.2.0]hept-2-ene-2-carboxylic acid (100 mg).

IR (Nujol): 3350-3050, 1730-1770 cm$^{-1}$

NMR (D$_2$O, δ): 1.21 (3H, d, J=7 Hz), 1.28 (3H, d, J=8 Hz), 1.5-2.0 (1H, m), 2.5-2.9 (1H, m)

Example (7-7)

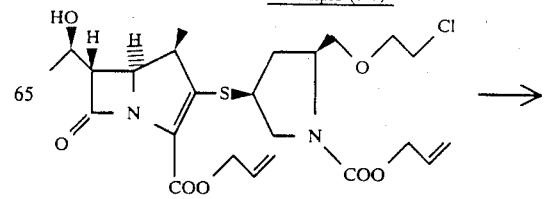

-continued

Example (7-7)

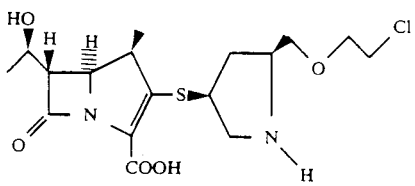

To a solution of allyl (4R,5S,6S)-3-[(2S,4S)-1-allyloxycarbonyl-2-(2-chloroethyloxymethyl)pyrrolidin-4-yl]thio-6-[(1R)-1-hydroxyethyl]-4-methyl-7-oxo-1-azabicyclo[3.2.0]hept-2-ene-2-carboxylate (0.28 g), triphenylphosphine (0.015 g) and dimedone (0.16 g) in a mixture of 4-methyl-2-pentanone (3.36 ml), ethanol (1.68 ml) and water (0.14 ml) was added triphenylphosphine)palladium(0) (30 mg) at ambient temperature in a stream of nitrogen. The mixture was stirred at the same condition for 5 hours to give a solid. The solid was collected by filtration to give (4S,5S,6S)-3-[(2S,4S)-2-(2-chloroethyloxymethyl)pyrrolidine-4-yl]thio-6-[(1R)-1-hydroxyethyl]-4-methyl-7-oxo-1-azabicyclo[3.2.0]hept-2-ene-2-carboxylic acid (0.055 g).

mp: 170° C. (dec.)
IR (KBr): 1760–1720 cm$^{-1}$
NMR (CDCl$_3$, δ): 1.20 (3H, d, J=7.5 Hz), 1.28 (3H, d, J=7.5 Hz)
FAB-MS: 405, 407 (M$^+$ +1)

Example 8

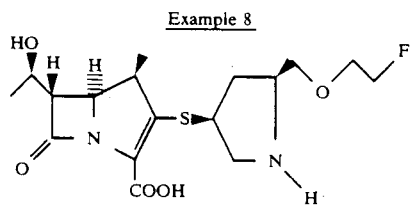

Acetone (5.0 ml) was dropwise added to a solution of the compound obtained in Example 7-6) (0.53 g) in water (0.8 ml) at 0°–10° C. with stirring. The precipitates were collected by filtration to give (4R,5S,6S)-3-[(2S,4S)-2-(2-fluoroethyloxymethyl)pyrrolidin-4-yl]thio-6-[(1R)-1-hydroxyethyl]-4-methyl-7-oxo-1-azabicyclo[3.2.0]hept-2-ene-2-carboxylic acid as a crystal (0.47 g).

mp : 180° C. (dec.)
IR (Nujol): 3350–3050, 1760, 1735 cm$^{-1}$
NMR (D$_2$O, δ): 1.21 (3H, d, J=7 Hz), 1.28 (3H, d, J=8 Hz)

Example 9

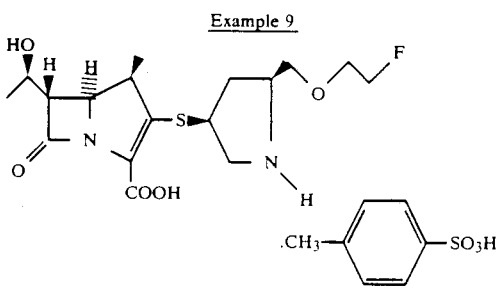

A solution of (4R,5S,6S)-3-[(2S,4S)-2-(2-fluoroethyloxymethyl)pyrrolidin-4-yl]thio-1R)-1-hydroxyethyl]-4-methyl-7-oxo-1-azabicyclo[3.2.0]hept-2-ene-2-carboxylic acid (0.20 g) and p-toluenesulfonic acid monohydrate (0.075 g) in water (10 ml) was lyophilized to give p-toluenesulfonic acid salt of (4R,5S,6S)-3-[(2S,4S)-2-(2-fluoroethyloxymethyl)pyrrolidin-4-yl]thio-6-[(1R)-1-hydroxyethyl]-4-methyl-7-oxo-1-azabicyclo[3.2.0]hept-2-ene-2-carboxylic acid (0.26 g).

mp: 95° C. (dec.)
IR (KBr): 1760–1745 cm$^{-1}$

Example 10

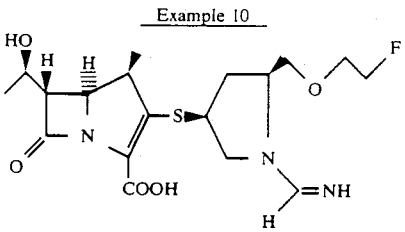

To a solution of (4R,5S,6S)-3-[(2S,4S)-2-(2-fluoroethyloxymethyl)pyrrolidin-4-yl]thio-6-[(1R)-1-hydroxyethyl]-4-methyl-7-oxo-1-azabicyclo[3.2.0]hept-2-ene-2-carboxylic acid (0.3 g) in water (90 ml) was added benzyl formimidate hydrochloride (0.4 g) under ice-cooling with stirring, keeping the pH between 8.5–9 with 4N aqueous sodium hydroxide. After stirring for 30 minutes, the mixture was adjusted to pH 6.5 with 1N hydrochloric acid and washed with ethyl acetate (60 ml×3). The aqueous layer was subjected to a column chromatography on nonionic adsorption resin, "Diaion HP-20" (10 ml), washed with water, eluted with a mixture of acetone and water (7:93 V/V), and lyophilized to give (4R,5S,6S)-3-[(2S,4S)-2-(2-fluoroethyloxymethyl)-1-formimidoylpyrrolidin-4-yl]thio-6-[(1R)-1-hydroxyethyl]-4-methyl-7-oxo-1-azabicyclo[3.2.0]hept-2-ene-2-carboxylic acid [0.2 g].

mp: 165° C. (dec.)
IR (KBr): 1760–1735, 1710–1700, 1595–1580 cm$^{-1}$
NMR (D$_2$O, δ): 1.18 (3H, d, J=7.5 Hz), 2.07 (3H, d, J=7 Hz), 7.98 (1H, s)
FAB-MS: 416 (M$^+$ +1)

Example 11

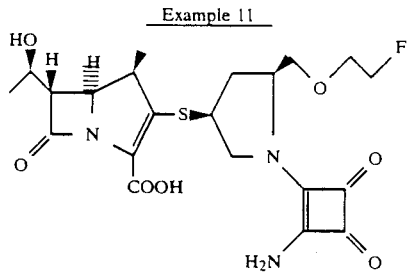

To a solution of (4R,5S,6S)-3-[(2S,4S)-2-(2-fluoroethyl)oxymethylpyrrolidin-4-yl]thio-6-[(1R)-1-hydroxyethyl[-4-methyl-7-oxo-1-azabicyclo[3.2.0]hept-2-ene-2carboxylic acid (0.4 g) in water (20 ml) was added 2-amino-1-ethoxy-3,4-dioxo-1-cyclobutene (320 mg) at 10°–15° C. with stirring, keeping the pH between 8.2–8.7 with 4N aqueous sodium hydroxide solution. After one hour, the mixture was adjusted to pH 6 with 1N hydrochloric acid and washed with a mixture of ethyl acetate and tetrahydrofuran (1:1 V/V) (30 ml×6). The aqueous solution was subjected to a column chromatography on nonionic adsorption resin, "Diaion HP-20" (20 ml), which was washed with water and eluted with a mixture of acetone and water (7:93 V/V). The fractions containing the desired compound were collected and lyophilized to give (4R,5S,6S)-3-[(2S,4S)-1-(2-amino-3,4-dioxo-1-cyclobuten-1-yl)-2-(2-fluoroethyl)oxymethylpyrrolidin-4-yl]thio-6-[(1R)-1-hydroxyethyl]-4-methyl-7-oxo-1-azabicyclo[3.2.0]hept-2-ene-2-carboxylic acid (0.38 g).

mp: 200° C. (dec.)

IR (KBr): 1750-1720 cm$^{-1}$

NMR (D$_2$O, δ): 1.22 (3H, d, J=7.5 Hz), 1.30 (3H, d, J=7.5 Hz)

What is claimed is:

1. A compound of the formula:

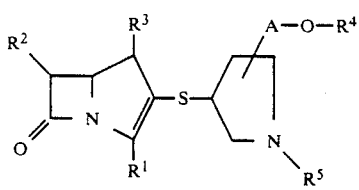

in which R$^1$ is carboxy or protected carboxy,
R$^2$ is hydroxy(lower)alkyl or protected hydroxy(lower)alkyl,
R$^3$ is hydrogen or lower alkyl,
R$^4$ is 2-fluoroethyl, 2-chloroethyl, 2-fluoropropyl or 4-fluorobuty
R$^5$ is hydrogen, lower alkanimidoyl, unsubstituted lower cycloalkenyl or substituted by a group consisting of oxo and amino, or imino-protective group, and
A is lower alkylene, or pharmaceutically acceptable salts thereof.

2. A compound of claim 1, wherein
R$^1$ is carboxy or pharmaceutically acceptable esterified carboxy,
R$^2$ is hydroxy(lower)alkyl, acyloxy(lower)alkyl, mono- (or di or tri)phenyl(lower)alkoxy(lower)alkyl, tri(lower)alkylsilyloxy(lower)alkyl, triphenylsilyloxy(lower)alkyl or triphenylsilyloxy(lower)alkyl and
R$^5$ is hydrogen, lower alkanimidoyl; unsubstituted lower cycloalkenyl or substituted by a group consisting of oxo and amino; or acyl.

3. A compound of claim 2, wherein
R$^1$ is carboxy, phenyl(or nitrophenyl)(lower)alkoxycarbonyl or lower alkenyloxycarbonyl,
R$^2$ is hydroxy(lower)alkyl, or carbonyloxy(lower)alkyl, (lower)alkenyloxycarbonyl(lower)alkyl or oxy(lower)alkyl, and
R$^5$ is hydrogen, lower alkanimidoyl, 3-oxo(C$_3$-C$_6$)-cycloalkenyl substituted by a group consisting of amino and oxo, lower alkenyloxycarbonylimino or phenyl(or nitrophenyl)(lower)alkoxycarbonylimino.

4. A compound of claim 3, wherein
R$^1$ is carboxy,
R$^2$ is hydroxy(lower)alkyl,
R$^5$ is hydrogen, lower alkanimidoyl or 2-amino-3-oxo(C$_3$-C$_6$)cycloalkenyl substituted by oxo.

5. A compound of claim 4, wherein
R$^3$ is lower alkyl.

6. A compound of claim 5, wherein
R$^1$ is carboxy,
R$^2$ is hydroxy(C$_1$-C$_4$)alkyl,
R$^3$ is C$_1$-C$_4$ alkyl,
R$^5$ is hydrogen, C$_1$-C$_4$ alkanimidoyl or 2-amino-3-oxo-(C$_4$-C$_6$)cycloalkenyl substituted by oxo.

7. A compound of claim 6, wherein
R$^2$ is 1-hydroxyethyl,
R$^3$ is methyl,
R$^5$ is hydrogen, formimidoyl or 2-amino-3,4-dioxo-1-cyclobuten-1-yl.

8. A compound of claim 7, which is
(4R,5S,6S)-3-[(2S,4S)-2-(2-fluoroethyloxymethyl)-pyrrolidin-4yl-thio-6-[(1R)-1-hydroxyethyl]-4-methyl-7-oxo-1-azabicyclo[3.2.0]-hept-2-ene-2-carboxylic acid or its toluenesulfonate,
(4R,5S,6S)-2-[(2S,4S)-2-(2-fluoroethyloxymethyl)-1-formimidoylpyrrolidin-4-yl]thio-6-[(1R)-1-hydroxyethyl]-4-methyl-7-oxo-1-azabicyclo[3.2.0]hept-2-ene-2-carboxylic acid, or
(4R,5S,6S)-3-[(2S,4S)-1-(2-amino-3,4-dioxo-1-cyclobuten-1-yl)-2-(2-fluoroethyl)oxymethylpyrrolidin-4-yl]thio-6-[(1R)-1-hydroxyethyl]-4-methyl-7-oxo-1-azabicyclo[3.2.0]hept-2-ene-2-carboxylic acid.

9. An antibacterial pharmaceutical composition comprising, as an active ingredient, an antibacterially effective amount of a compound of claim 1, in admixture with a pharmaceutically acceptable carrier or excipient.

10. A method for the treatment of infectious diseases caused by pathogenic bacteria which comprises administering an antibacterially effective amount of a compound of claim 1 to a human being or animal.

* * * * *

UNITED STATES PATENT AND TRADEMARK OFFICE
CERTIFICATE OF CORRECTION

PATENT NO. : 4,983,596
DATED : JANUARY 8, 1991
INVENTOR(S) : MASAYOSHI MURATA ET AL

It is certified that error appears in the above-identified patent and that said Letters Patent is hereby corrected as shown below:

Column 7, line 65, after "er)alkyl" insert --"--.

Column 9, line 29, after "N-alkylcarbamoyl", change "[" to --(--.

Column 10, line 46, indent and start new paragraph with --(1) Process 1--.

Column 18, line 6, change "$R_a^4$" to --$R_b^4$--.

Column 19, line 6, change "blow" to --below--;
line 12, change "mg/ml" to --µg/ml--;
line 43, delete "a" (first occurrence), insert --the--.

Column 25, line 7, after "(M+", insert --)--;
line 19, after "ymethyl-", insert --1--;
line 30, before "N-methyl", insert --{--
line 31, change "amino)" to --amino}--.

UNITED STATES PATENT AND TRADEMARK OFFICE
CERTIFICATE OF CORRECTION

PATENT NO. : 4,983,596
DATED : January 8, 1991
INVENTOR(S) : Masayoshi Murata, et al.

It is certified that error appears in the above-indentified patent and that said Letters Patent is hereby corrected as shown below:

Column 26, line 2, after "2", delete "35".

Column 29, line 61, after "separated" insert --,--.

Column 30, line 3, after "(1H, M" delete "}" and insert
    --)--;
        line 6, change "{25,4R)" to --(25,4R)--;
        line 22, after "J=7" delete "250";
        lines 48-49, change "oxymethyl14" to
    --oxymethyl-4--;
        line 68, after "thereto", insert --.--.

Column 31, lines 14-15, change "(1H.m)" to --(1H.gm)--;
        line 52, after "evaporated" insert --.--.

Column 36, Example 1-3, change " 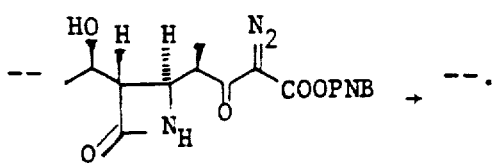 " to
-- 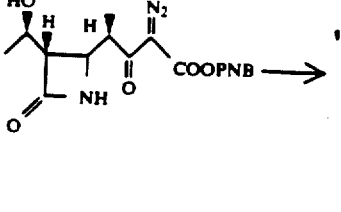 --.

Column 33, line 45, change "1750 CM⁻¹ NMR (CDCl3" to
    --1750 CM⁻¹NMR (CDCl$_3$--.

UNITED STATES PATENT AND TRADEMARK OFFICE
CERTIFICATE OF CORRECTION

PATENT NO. : 4,983,596

DATED : JANUARY 8, 1991

INVENTOR(S) : MASAYOSHI MURATA ET AL

It is certified that error appears in the above-identified patent and that said Letters Patent is hereby corrected as shown below:

Column 36, line 32, after "thio-7-oxo-1", insert -- - --;
       line 64, change "ethyloxmethyl" to
  --ethyloxymethyl--.

Column 37, line 66, change "10°-5°C" to --10°~5°C.

Column 39, line 49, change "4R,5S,6S}" to --4R,5S,6S)--;
       line 50, before "(2S,4S-2-", insert --[--;
       lines 50-51, after "pyrrolidin", insert -- - --.

Column 40, line 22, after "tetrahydrofuran", insert --.--;
       line 25, after "solvent", insert --.--;
       line 30, after "solution", insert --.--
       line 37, after "up: 90°C.(dec)", start new sentence
  and add --IR(KBr): $1720 cm^{-1}$--
       line 60, change "(4R,5S.6S)" to --(4R,5S,6S)--.

Column 41, line 24, change "1azabicyclo" to --1-azabicyclo--;
       line 40, change "[60 ml}" to --[60 ml]--;
       line 50, after "($M^{+}+1$", insert --)--.

Column 42, line 12, change "were" to --was--;
       line 66, change "were" to --was--.

Column 44, line 68, after "nyl-2-", insert --(--.

UNITED STATES PATENT AND TRADEMARK OFFICE
CERTIFICATE OF CORRECTION

PATENT NO. : 4,983,596
DATED : JANUARY 8, 1991
INVENTOR(S) : MASAYOSHI MURATA ET AL

It is certified that error appears in the above-identified patent and that said Letters Patent is hereby corrected as shown below:

Column 46, lines 14-15, change "allyloxycarbonyl" to
   --alloyloxy-carbonyl--;
      line 27, change "[(2S,4)" to --[(2S,4S)--.

Column 47, lines 51-52, change "(2-fluoroethyloxymethyl)" to
   --(2-fluro-ethyloxymethyl)--.

Column 48, line 41, after "hydroxyethyl", insert --]--.

Column 49, line 23, after "(2S,4S)-1-al", insert -- - --;
      line 64, after "(1R)-1-al", insert -- - --.

Column 51, line 18, after "added", insert --tetrahis--;
      line 22, change "(4S,5S,6S)" to --(4R,5S,6S)--;
      line 67, after "thio-", insert --6-[(--.

Column 53, line 27, change "fluorobuty" to --fluorobutyl--;
      line 41, change "triphenylsilyloxy" to
   --tribenzylsilyoxy--;
      line 53, after "hydrogen", delete "," and
   insert --;--.

UNITED STATES PATENT AND TRADEMARK OFFICE
CERTIFICATE OF CORRECTION

PATENT NO. : 4,983,596
DATED : January 8, 1991
INVENTOR(S) : Masayoshi Murata, et al.

It is certified that error appears in the above-indentified patent and that said Letters Patent is hereby corrected as shown below:

```
Column 54, line 1, delete "or", insert --[phenyl (or
     nitrophenyl)-(lower)alkoxy]--.
```

Signed and Sealed this

Fifth Day of April, 1994

Attest:

BRUCE LEHMAN

Attesting Officer

Commissioner of Patents and Trademarks